(12) United States Patent
Lombardi et al.

(10) Patent No.: US 8,481,446 B2
(45) Date of Patent: Jul. 9, 2013

(54) CHEMICALLY-RESISTANT COATING COMPOSITION

(76) Inventors: John L. Lombardi, Tucson, AZ (US); Chuchawin Changtong, Tucson, AZ (US)

( * ) Notice: Subject to any disclaimer, the term of this patent is extended or adjusted under 35 U.S.C. 154(b) by 352 days.

(21) Appl. No.: 12/652,670

(22) Filed: Jan. 5, 2010

(65) Prior Publication Data

US 2010/0279850 A1 Nov. 4, 2010

Related U.S. Application Data

(63) Continuation-in-part of application No. 11/779,239, filed on Jul. 17, 2007, now Pat. No. 7,642,215, which is a continuation of application No. 10/931,121, filed on Aug. 30, 2004, now Pat. No. 7,259,122.

(51) Int. Cl.
*B01J 31/02* (2006.01)
*C07F 7/18* (2006.01)
*C07F 7/22* (2006.01)

(52) U.S. Cl.
USPC .......... 502/158; 502/159; 556/440; 556/420; 556/436; 556/427; 556/413; 556/446; 556/9; 556/173

(58) Field of Classification Search
None
See application file for complete search history.

(56) References Cited

U.S. PATENT DOCUMENTS

| | | | |
|---|---|---|---|
| 4,247,456 A | 1/1981 | Von Brachel et al. | |
| 5,916,481 A * | 6/1999 | Willey | 252/186.21 |
| 2003/0022105 A1 | 1/2003 | Prasad et al. | |
| 2008/0153690 A1 | 6/2008 | Lombardi | |
| 2009/0005234 A1 | 1/2009 | Nakayam et al. | |
| 2009/0043065 A1 | 2/2009 | Khabashesku et al. | |

OTHER PUBLICATIONS

Lotus LADM Based Self-Decontaminating Surfaces, Published on May 1, 2007.*
PCT/US11/020281—International Search Report and Written Opinion dated Nov. 28, 2011.
PCT/US11/020281—Preliminary Report on Patentability dated Jul. 19, 2012.

* cited by examiner

*Primary Examiner* — Yun Qian
(74) *Attorney, Agent, or Firm* — Dale F. Regelman; Quarles & Brady LLP

(57) ABSTRACT

A coating composition comprising a Photocatalyst Composition comprising a photocatalyst and a pendent silyl ester group, wherein the photocatalyst produces singlet oxygen in the presence of light and ambient air. In certain embodiments, the coating composition further comprises a singlet oxygen scavenger.

9 Claims, 10 Drawing Sheets

Plot between ln[200A] Vs time (sec)

Plot between ln[200B] Vs time (sec)

Plot between ln[200C] Vs time (sec)

Plot between ln[200D] Vs time (sec)

Plot between ln[300A] Vs time (sec)

Plot between ln[300B] Vs time (sec)

Plot between ln[300C] Vs time (sec)

Plot between ln[300D] Vs time (sec)

Plot between ln[400A] Vs time (sec)

Plot between ln[200E] Vs time (sec)

CHEMICALLY-RESISTANT COATING COMPOSITION

CROSS-REFERENCE TO RELATED APPLICATIONS

This Application is a Continuation In Part Application claiming priority from a United States Utility Application having Ser. No. 11/779,239, now U.S. Pat. No. 7,642,215, which claimed priority from a United States Utility Application having Ser. No. 10/931,121 filed Aug. 30, 2004 now U.S. Pat. No. 7,259,122.

GOVERNMENT LICENSE RIGHTS

The U.S. Government has a paid-up license in this invention and the right in limited circumstances to require the patent owner to license others on reasonable terms as provided by the terms of "Lightweight and Low Cost Flexible Structure Textiles" U.S. Army Phase I Small Business Innovation Research Grant Contract No. DAAD16-03-C-0011.

FIELD OF THE INVENTION

The invention relates to a coating composition that is resistant to, and that decontaminates, toxic chemical and/or biological agents.

BACKGROUND OF THE INVENTION

Exposure to toxic chemical and biological agents ("CBAs") is a growing concern to both military and civilian organizations alike. Areas of enhanced vulnerability include assemblies of persons, whether military or civilian. One such scenario includes military personnel assembled within one or more tents and/or portable shelters.

In order to mitigate the harmful effects of an exposure to CBA agents, many military shelters are constructed from fabrics which include one or more polymeric materials exhibiting barrier properties to one or more toxic agents. Many of these fabrics comprise, for example, fluoropolymers such a polytetrafluoroethylene ("PTFE"). One such composite material comprises Teflon coated Kevlar. While such composites demonstrate acceptable barrier properties, these CBA barrier shelter fabrics are expensive and require multiple manufacturing operations to join various fabric segments. The high costs of materials in combination with high manufacturing costs limit the availability of such prior art fabrics for widespread use.

As a result, most real-world military shelters are not made from such fabrics. Rather, current shelters are formed using materials having inferior CBA resistance. For example, forces of the United States of America typically utilize a General Purpose Shelter Fabric ("GP Fabric") manufactured from cloth coated with polyvinyl chloride ("PVC"). GP Fabric is relatively inexpensive and affords soldiers adequate protection against inclement weather including rain, snow, wind, and dust storms. Shelters made from GP Fabric, however, offer minimal CBA protection. Such prior art shelters require an additional M28 Saranex liner to impart acceptable CBA barrier properties. As those skilled in the art will appreciate, use of such liners adds to the overall weight, cost, and complexity, of the shelter.

Applicants' invention includes a more convenient, lower cost means of providing CBA resistance comprising disposing a waterborne coating composition onto various fabrics used to manufacture shelters, clothing, masks, and the like.

Applicants' coating composition may be applied using conventional coating methods, such as knife coating, spray coating, calendaring, and the like. Waterborne coatings are desirable because of inherent low toxicity and low flammability properties. Applicants' coating solutions rapidly and uniformly spread over the fabric/substrate surfaces, including the seams, thereby producing a continuous CBA barrier film after drying. Applicants' coating effectively "hardens" the shelter, i.e. enhances its CBA barrier properties.

BRIEF DESCRIPTION OF THE DRAWINGS

The invention will be better understood from a reading of the following detailed description taken in conjunction with the drawings in which like reference designators are used to designate like elements, and in which.

SUMMARY OF THE INVENTION

Figure 1:
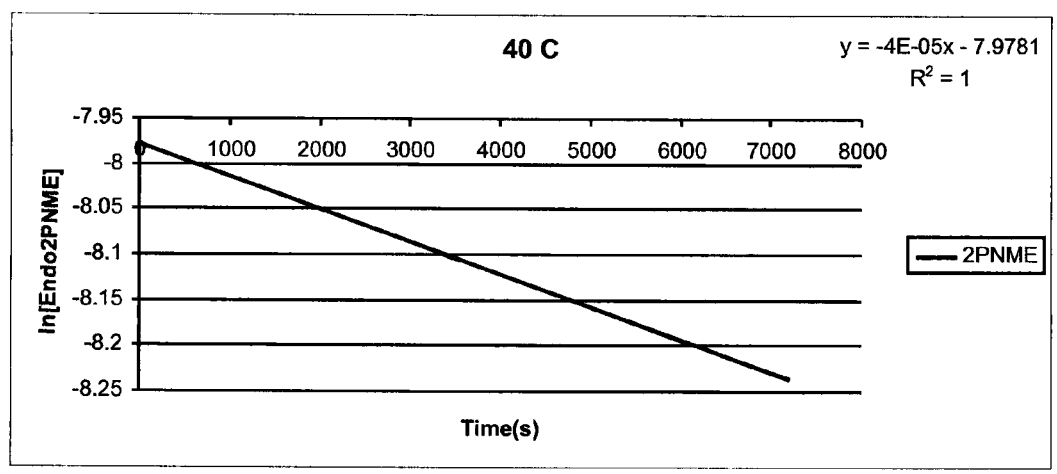
FIG. 1 graphically shows the rate of decomposition of a first Endoperoxide compound to release singlet oxygen.

In certain embodiments, Applicants' invention includes a coating composition comprising a Photocatalyst Composition comprising a photocatalyst and a pendent silyl ester group, wherein the photocatalyst produces singlet oxygen in the presence of light and ambient air. In certain embodiments, Applicants' coating composition further comprises a singlet oxygen scavenger.

DETAILED DESCRIPTION OF THE PREFERRED EMBODIMENTS

Applicants have developed Photocatalyst Compositions which become highly photoactive upon exposure to visible light and generate singlet oxygen from ambient air. Singlet oxygen has been shown to be a very effective oxidizing agent capable of decomposing both toxic chemicals as well as numerous biological pathogens/microbial species. The high chemical stability of t Applicants' photocatalyst compositions enables them to continually produce singlet oxygen over a long time period without losing activity. Applicants have found these compounds to be effective for oxidizing CBA compounds.

Applicants' coating composition generates singlet oxygen using Reaction Scheme "A", below. Upon absorption of light, the photocatalyst undergoes electronic excitation to a singlet state followed by electron reorganization to form the excited triplet state. Triplet photocatalyst transfers energy to ambient triplet oxygen to form reactive singlet oxygen. The singlet oxygen generated ($^1O_2$), is the reactive species capable of oxidizing and decontaminating CBAs.

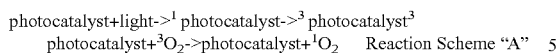

Reaction Scheme "A"

In various embodiments, Applicants' Photocatalyst Composition III comprises a Photocatalyst I and one or more pendant silyl ester groups II. In certain embodiments, (n) is greater than or equal to 1 and less than or equal to 4. In certain embodiments, (m) is greater than or equal to 1 and less than or equal to 3. In certain embodiments, R is selected from the group consisting of methyl, ethyl, and propyl. Such pendant silyl ester groups facilitate formation of a stable covalent attachment of Applicants' Photocatalyst Composition to a wide variety of surfaces. Further Applicants' photocatalyst compositions have a high affinity for aluminum surfaces which enable those photocatalyst compositions to be used in aircraft paints.

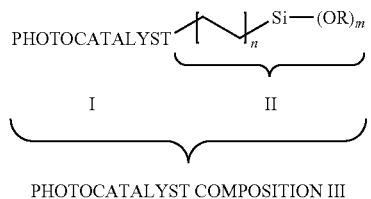

In various embodiments, Applicants react a substituted Photocatalyst I with one or more of silyl ester compounds 4, 5, 6, 7, and/or 8, to covalently bond one or more pendant silyl ester functionalities II to form Photocatalyst Composition III.

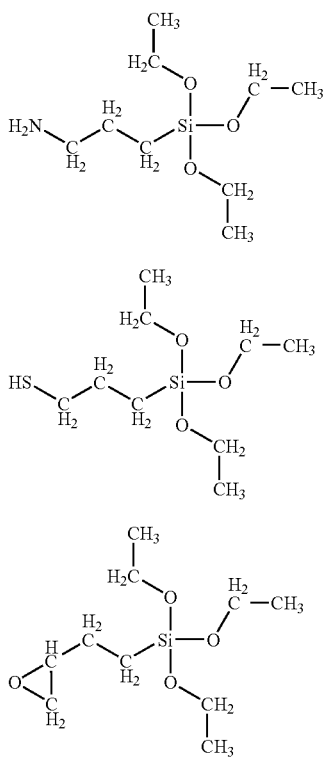

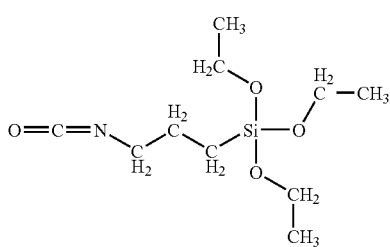

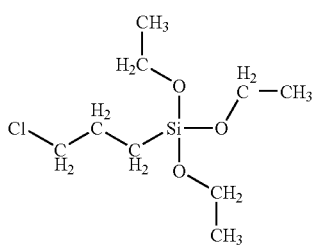

In various embodiments, Applicants' Photocatalyst Composition III comprises a substituted photocatalyst selected from the group consisting of substituted Acetonaphthones, substituted Acetophenonse, substituted Acridines, substituted Anthracenes, substituted Anthraquinones, substituted Anthrones, substituted Azulenes, substituted Benzils, substituted Benzophenones, substituted Benzopyranones, substituted Benzoquinones, substituted Flavones, substituted Camphoroquinone, substituted Chrysenes, substituted 7-Dehydrocholesterols, substituted Ergosterols, substituted Fluorenes, substituted Fluorenones, substituted Eosins, substituted Fluoresceins, substituted Phloxines, substituted Rose Bengals, substituted Erythrosins, substituted Indoles, substituted Naphthalenes, substituted Phenanthrenes, substituted Phenazines, substituted Thionines, substituted Azures, substituted Toluidine Blue, substituted Methylene Blues, substituted Pyrenes, substituted Quinoxalines, substituted Retinols, substituted Riboflavins, substituted Rubrenes, substituted Bacteriochlorophylls, substituted Chlorophylls, substituted Pheophytins, substituted Pheophorbides, substituted Protochlorophylls, substituted Coproporphyrins, substituted Fullerenes, substituted Porphyrins, substituted Metallo Porphyrins, substituted Porphines, substituted Rubrenes, and substituted Phthalocyanines, Examples 1 through 42 summarize the preparations of Photocatalyst Compositions 21, 22, 23, 24, 25, 27, 28, 29, 30, 32, 33, 36, 37, 39, 40, 43, 44, 46, 47, 48, 50, 51, 52, 54, 55, 56, 57, 59, 60, 62, 64, 65, 66, 68, 69, 70, 72, 73, 74, 76, 77, 78, 80, 81, 82, 84, 85, 86, 88, 89, 91, 92, 93, 94, 96, 97, 99, 100, 101, 103, 104, 106, 107, 108, 110, 111, 112, 114, 115, 116, 118, 119, 120, 122, 123, 124, 126, 127, 129, 130, 131, 133, 134, 136, 137, 138, 140, 141, 142, 144, 145, 146, 148, 149, 150, 152, 153, 155, 157, 159, 161, 163, 165, 167, 169, 171, 173, 175, 177, 179, 181, 183, 184, 186, 188, and 189. Examples 1-42 are presented to further illustrate to persons skilled in the art how to make and use the invention. These examples are not intended as a limitation, however, upon the scope of the invention, which is defined by the scope of the claims appended hereto.

EXAMPLE 1

Acetonaphthone CAS: 93-08-3; Φ~0.5-0.7

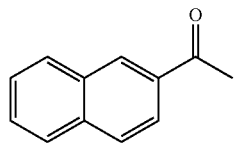

Reaction of substituted Acetonaphthone Photocatalyst 20A with aminosilyl ester 4 gives substituted Acetonaphthone Photocatalyst Composition 21. Reaction of substituted Acetonaphthone Photocatalyst 20A with mercaptosilyl ester 5 gives substituted Acetonaphthone Photocatalyst Composition 22.

Reaction of substituted Acetonaphthone Photocatalyst 20B with aminosilyl ester 4 gives substituted Acetonaphthone Photocatalyst Composition 21. Reaction of substituted Acetonaphthone Photocatalyst 20B with mercaptosilyl ester 5 gives substituted Acetonaphthone Photocatalyst Composition 22.

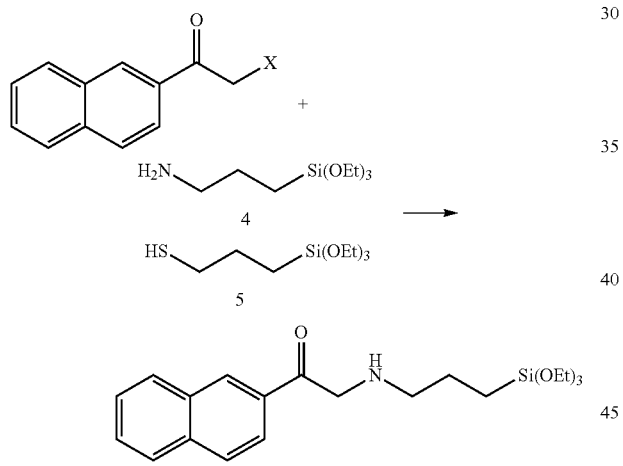

20A X = Cl; CAS: 50846-93-0
20B X = Br; CAS: 613-54-7

Reaction of substituted Acetonaphthone Photocatalyst 20C with epoxysilyl ester 6 gives substituted Acetonaphthone Photocatalyst Composition 23. Reaction of substituted Acetonaphthone Photocatalyst 20C with isocyanatosilyl ester 7 gives substituted Acetonaphthone Photocatalyst Composition 24. Reaction of substituted Acetonaphthone Photocatalyst 20C with chlorosilyl ester 7 gives substituted Acetonaphthone Photocatalyst Composition 25.

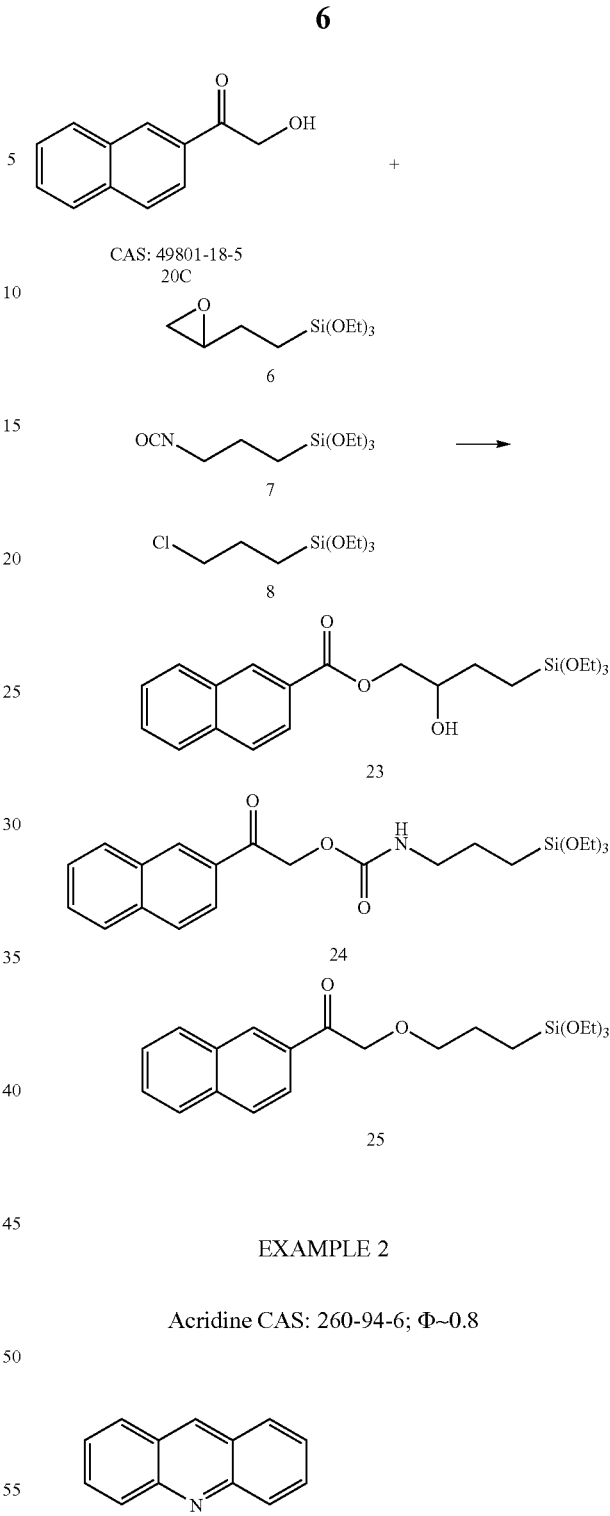

EXAMPLE 2

Acridine CAS: 260-94-6; Φ~0.8

Reaction of substituted Acridine photocatalyst 26A with epoxysilyl ester 6 gives substituted Acridine Photocatalyst Composition 29. Reaction of substituted photocatalyst 26A with isocyanatosilyl ester 7 gives Photocatalyst Composition 30.

Reaction of substituted photocatalyst 26B with epoxysilyl ester 6 gives Photocatalyst Composition 28. Reaction of substituted photocatalyst 26B with isocyanatosilyl ester 7 gives Photocatalyst Composition 27.

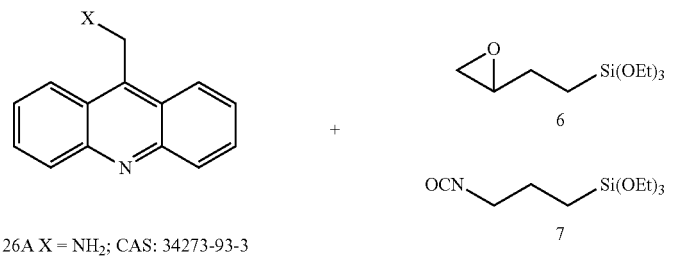
26A X = NH₂; CAS: 34273-93-3
26B X = OH; CAS: 35426-11-0
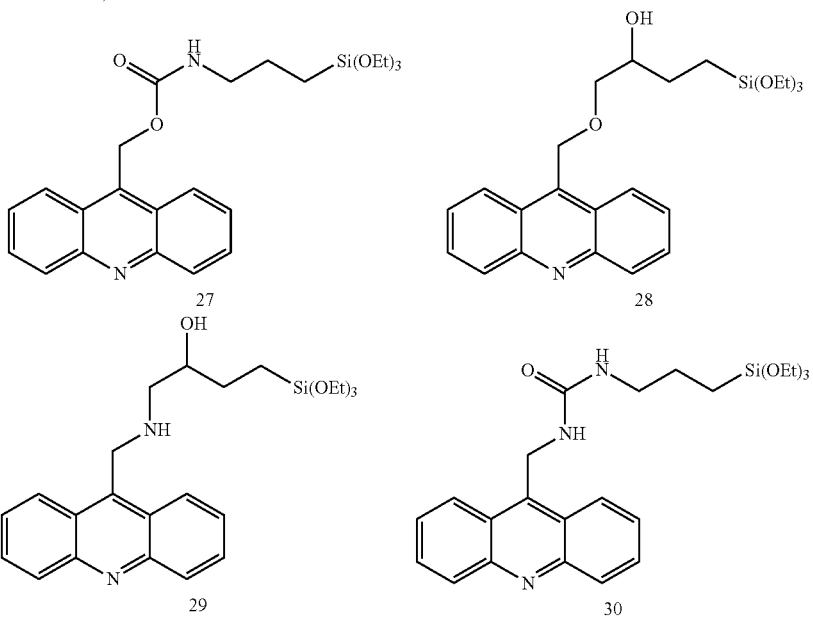
Reaction of substituted photocatalyst 31 with aminosilyl ester 4 gives Photocatalyst Composition 32. Reaction of substituted photocatalyst 31 with mercaptosilyl ester 5 gives Photocatalyst Composition 33.
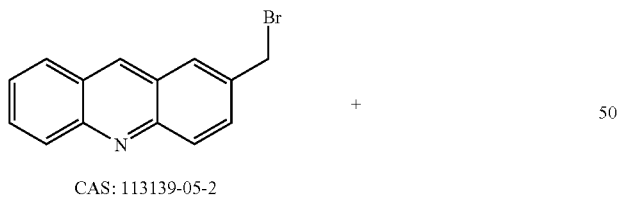
CAS: 113139-05-2
31
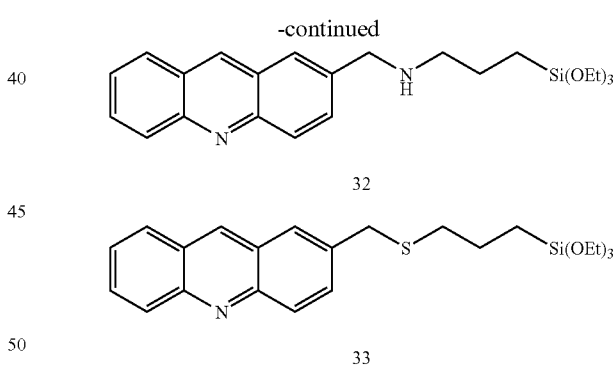
EXAMPLE 3
Flavone CAS: 525-82-6: Φ~0.5

Reaction of methyl substituted Flavone Photocatalyst 34 with N-bromo succinimide gives brominated Flavone Photocatalyst 35. Reaction of brominated substituted Flavone Photocatalyst 35 with aminosilyl ester 4 gives substituted Flavone Photocatalyst Composition 36. Reaction of brominated Flavone photocatalyst 35 with mercaptosilyl ester 5 gives substituted Flavone Photocatalyst Composition 37.

EXAMPLE 4

Camphoroquinone CAS 10373-78-1; Φ~0.8

Reaction of substituted Camphoroquinone Photocatalyst 38 with aminosilyl ester 4 gives substituted Camphoroquinone Photocatalyst Composition 39. Reaction of substituted Camphoroquinone Photocatalyst 38 with mercaptosilyl ester 5 gives substituted Camphoroquinone Photocatalyst Composition 40.

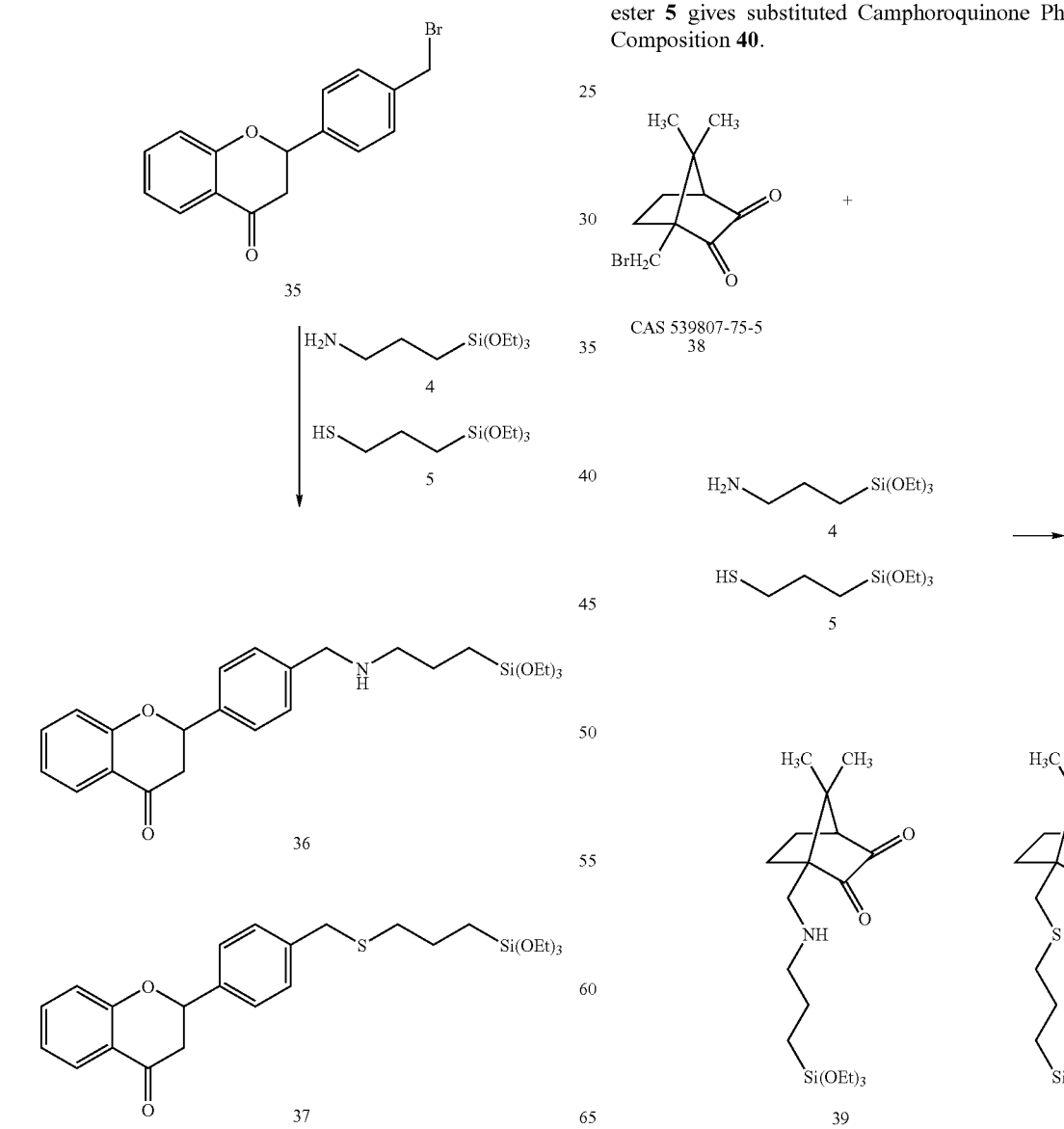

EXAMPLE 5

Chrysene CAS 218-01-9; Φ~0.6

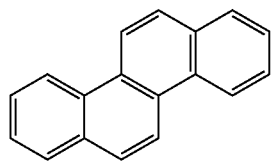

CAS 218-01-9

Bromination of substituted Chrysene Photocatalyst 41 gives brominated compound 42. Reaction of substituted Chrysene Photocatalyst 42 with aminosilyl ester 4 gives substituted Chrysene Photocatalyst Composition 43. Reaction of substituted Chrysene Photocatalyst 42 with mercaptosilyl ester 5 gives substituted Chrysene Photocatalyst Composition 44.

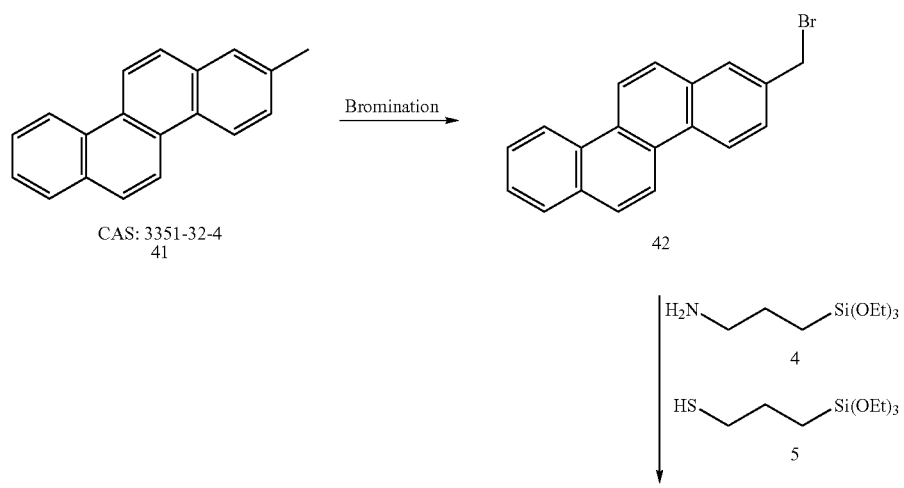

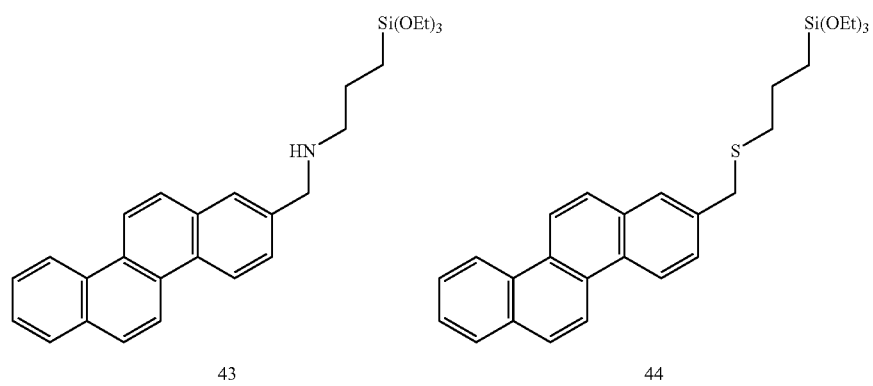

EXAMPLE 6

7-Dehydrocholesterol CAS: 434-16-2; Φ~0.8

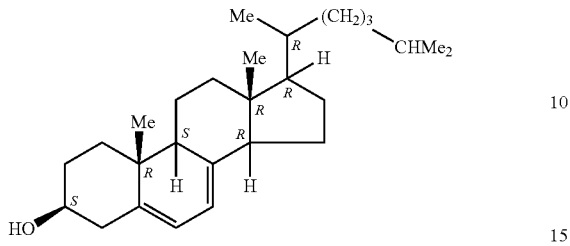

Reaction of substituted 7-Dehydrocholesterol photocatalyst 45 with epoxysilyl ester 6 gives substituted 7-Dehydrocholesterol Photocatalyst Composition 46. Reaction of substituted 7-Dehydrocholesterol Photocatalyst 46 with isocyanatosilyl ester 7 gives substituted 7-Dehydrocholesterol Photocatalyst Composition 47. Reaction of substituted 7-Dehydrocholesterol photocatalyst 45 with chlorosilyl ester 8 gives substituted 7-Dehydrocholesterol Photocatalyst Composition 48.

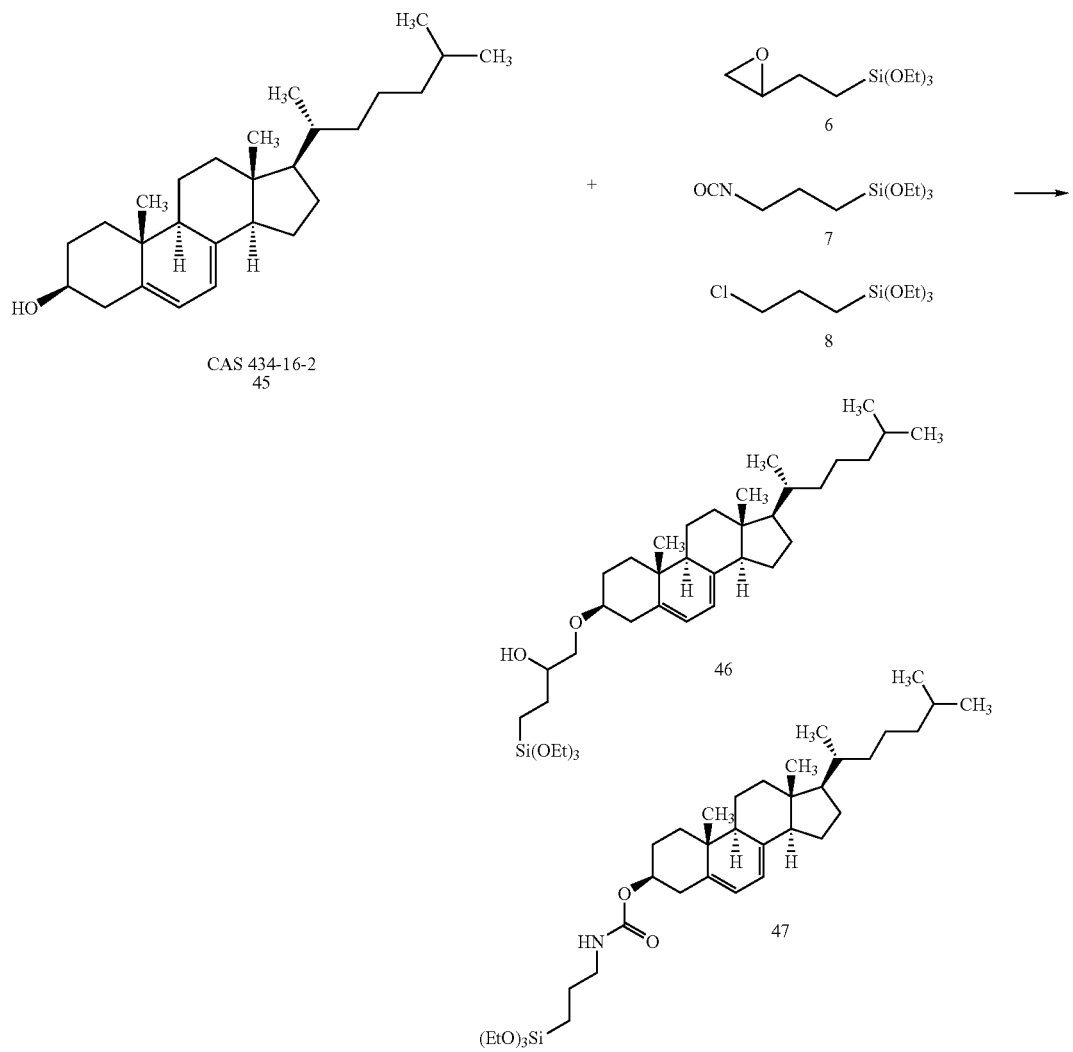

-continued

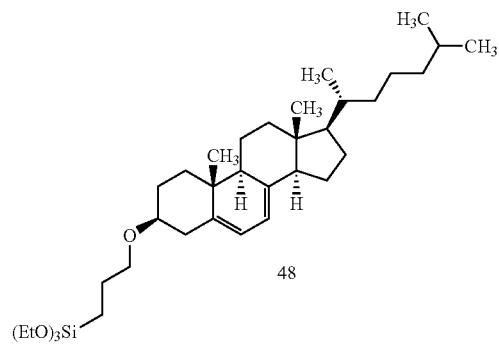

48

EXAMPLE 7

Ergosterol CAS: 57-87-4; Φ~0.8

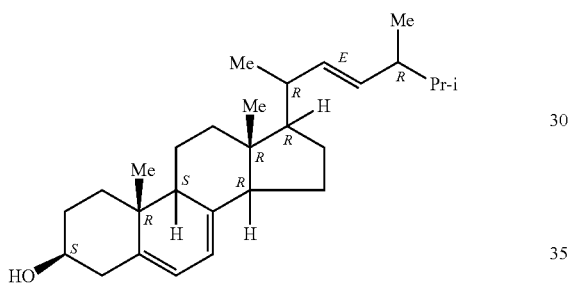

Reaction of substituted Ergosterol Photocatalyst 49 with epoxysilyl ester 6 gives substituted Ergosterol Photocatalyst Composition 50. Reaction of substituted Ergosterol Photocatalyst 49 with isocyanatosilyl ester 7 gives substituted Ergosterol Photocatalyst Composition 51. Reaction of substituted Ergosterol Pphotocatalyst 49 with chlorosilyl ester 8 gives substituted Ergosterol Photocatalyst Composition 52.

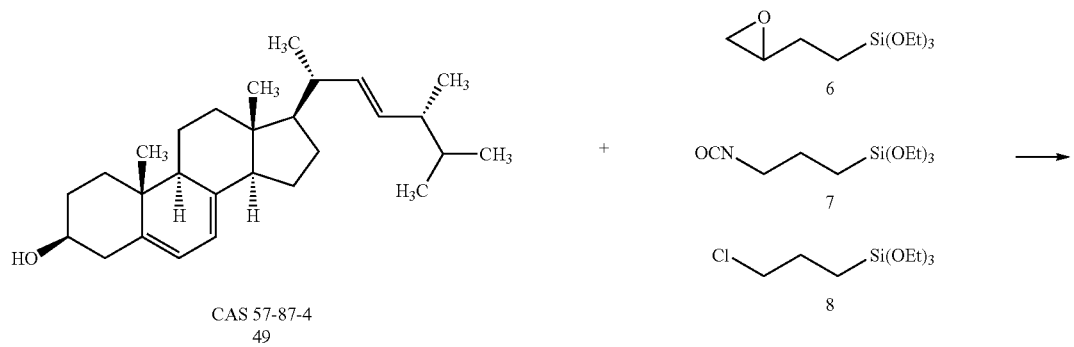

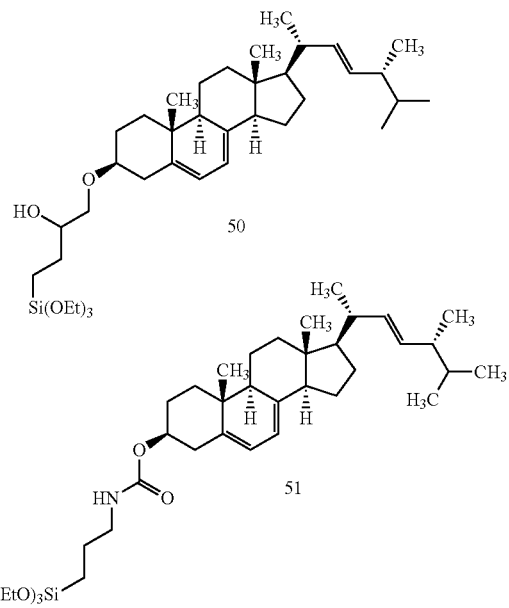

EXAMPLE 8

Fluorene CAS: 86-73-7; Φ~1

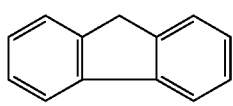

Reaction of substituted Fluorene Photocatalyst 53A with epoxysilyl ester 6 gives substituted Fluorene Photocatalyst Composition 54. Reaction of substituted Fluorene Photocatalyst 53A with isocyanatosilyl ester 7 gives substituted Fluorene Photocatalyst Composition 55.

Reaction of substituted Fluorene Photocatalyst 53B with epoxysilyl ester 6 gives substituted Fluorene Photocatalyst Composition 56. Reaction of substituted Fluorene Photocatalyst 53B with isocyanatosilyl ester 7 gives substituted Fluorene Photocatalyst Composition 57.

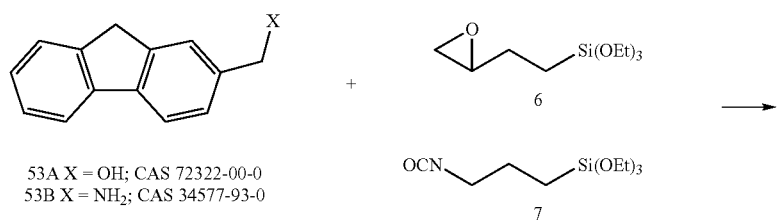

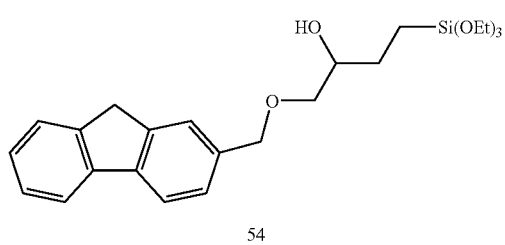
54
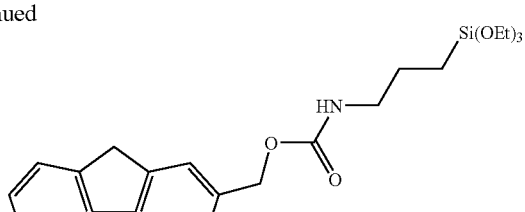
55
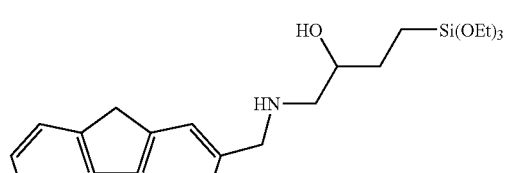
56
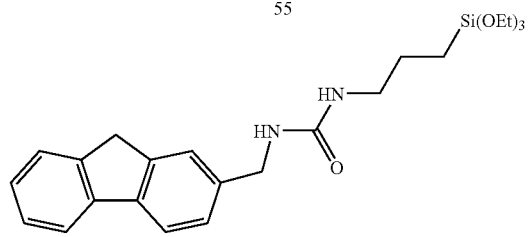
57
EXAMPLE 9
Fluorenone CAS: 486-25-9; Φ~0.8
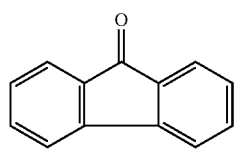 [SMILES: O=C1c2ccccc2-c2ccccc21]
Reaction of substituted Fluorenone Photocatalyst 58 with aminosilyl ester 4 gives substituted Fluorenone Photocatalyst Composition 59. Reaction of substituted Fluorenone Photocatalyst 58 with mercaptosilyl ester 5 gives substituted Fluorenone Photocatalyst Composition 60.
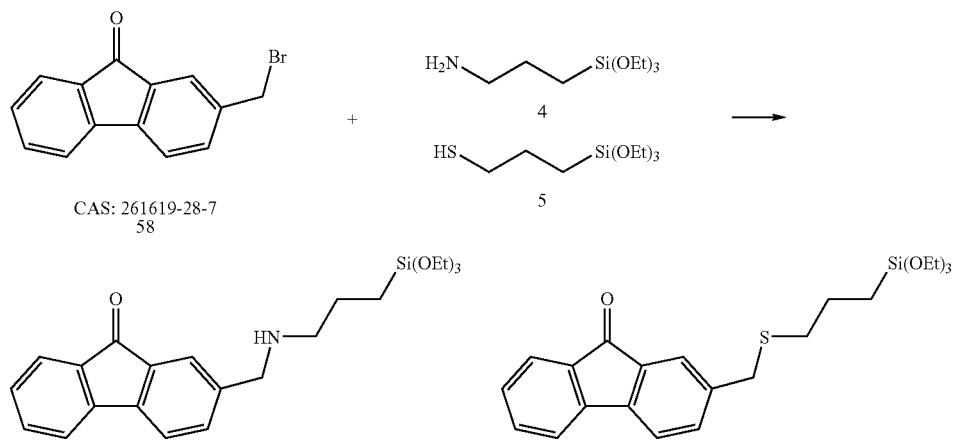

Reaction of substituted Fluorenone Photocatalyst 20B with aminosilyl ester 4 gives substituted Fluorenone Photocatalyst Composition 62.

EXAMPLE 10

Eosin B CAS: 548-24-3; Φ~0.3-0.5

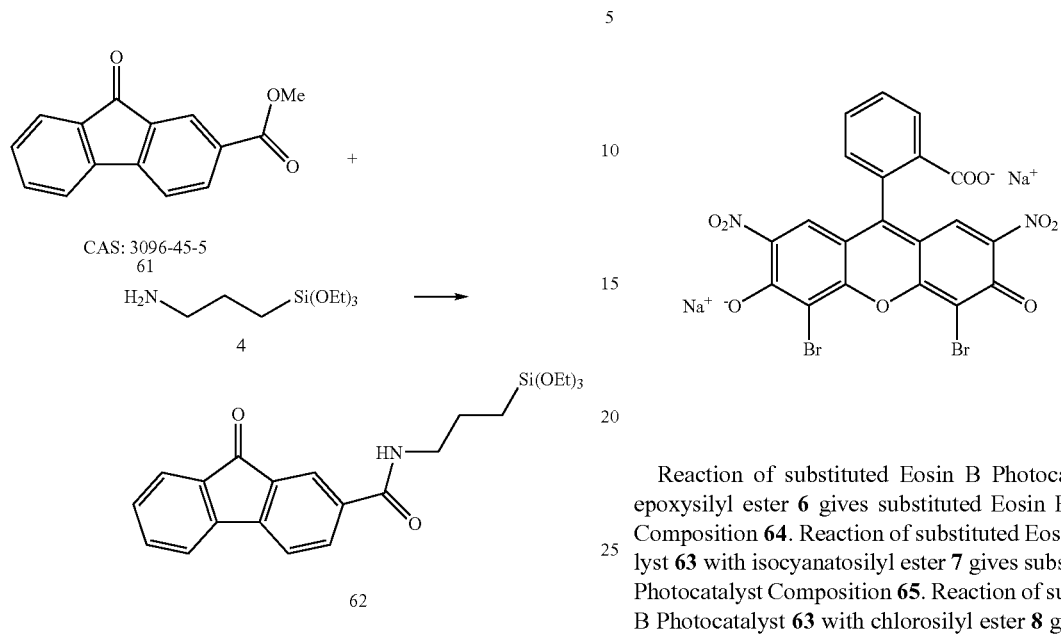

Reaction of substituted Eosin B Photocatalyst 63 with epoxysilyl ester 6 gives substituted Eosin B Photocatalyst Composition 64. Reaction of substituted Eosin B Photocatalyst 63 with isocyanatosilyl ester 7 gives substituted Eosin B Photocatalyst Composition 65. Reaction of substituted Eosin B Photocatalyst 63 with chlorosilyl ester 8 gives substituted Eosin B Photocatalyst Composition 66.

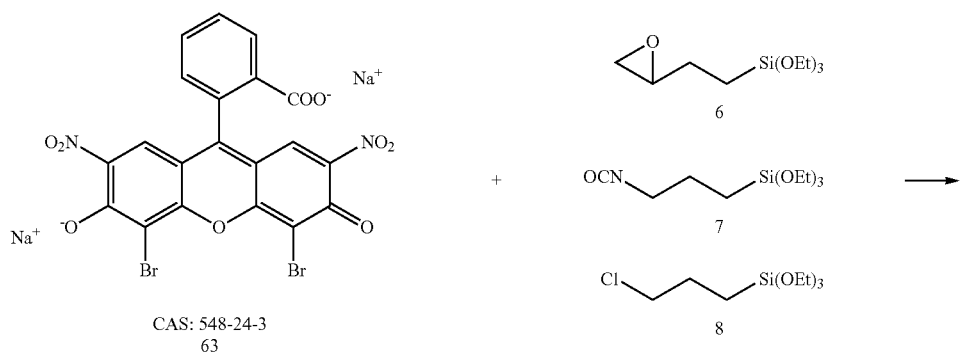

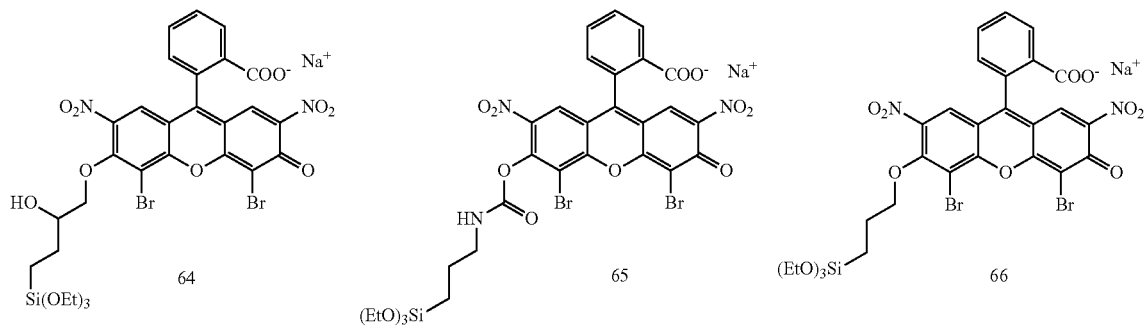

EXAMPLE 11

DiiodoFluorescein CAS: 33239-19-9; Φ~0.3-0.5

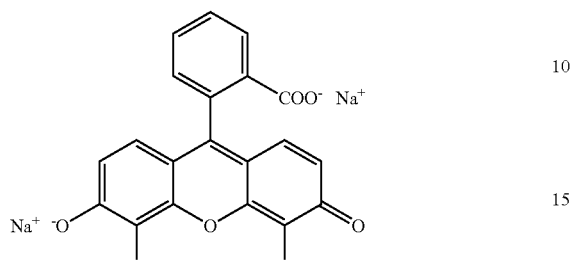

Reaction of substituted DiiodoFluorescein Photocatalyst 67 with epoxysilyl ester 6 gives substituted DiiodoFluorescein Photocatalyst Composition 68. Reaction of substituted DiiodoFluorescein Photocatalyst 67 with isocyanatosilyl ester 7 gives substituted DiiodoFluorescein Photocatalyst Composition 69 Reaction of substituted DiiodoFluorescein photocatalyst 67 with chlorosilyl ester 8 gives substituted DiiodoFluorescein Photocatalyst Composition 70.

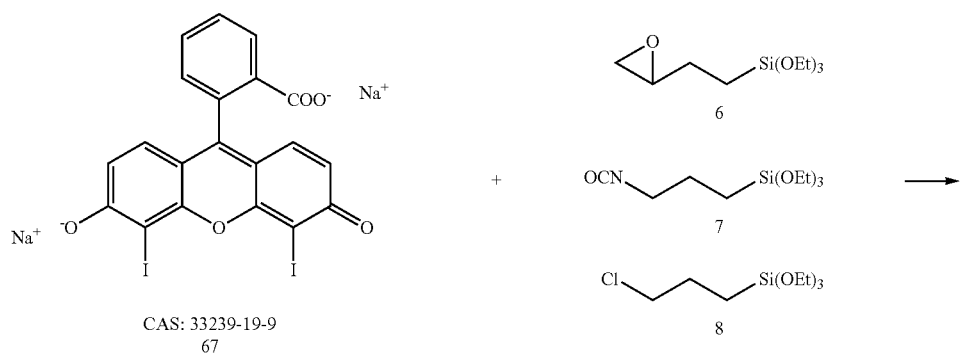

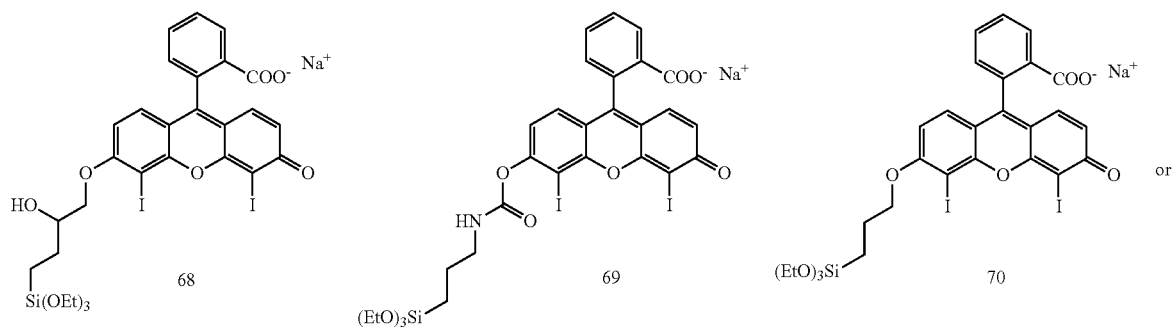

EXAMPLE 12

Eosin Y CAS: 17372-87-1; Φ~0.5-0.9

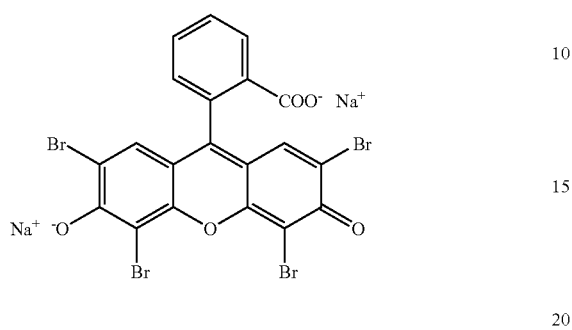

Reaction of substituted Eosin Y Photocatalyst 71 with epoxysilyl ester 6 gives substituted Eosin Y Photocatalyst Composition 72. Reaction of substituted Eosin Y Photocatalyst 71 with isocyanatosilyl ester 7 gives substituted Eosin Y Photocatalyst Composition 73. Reaction of substituted Eosin Y Photocatalyst 71 with chlorosilyl ester 8 gives substituted Eosin Y Photocatalyst Composition 74.

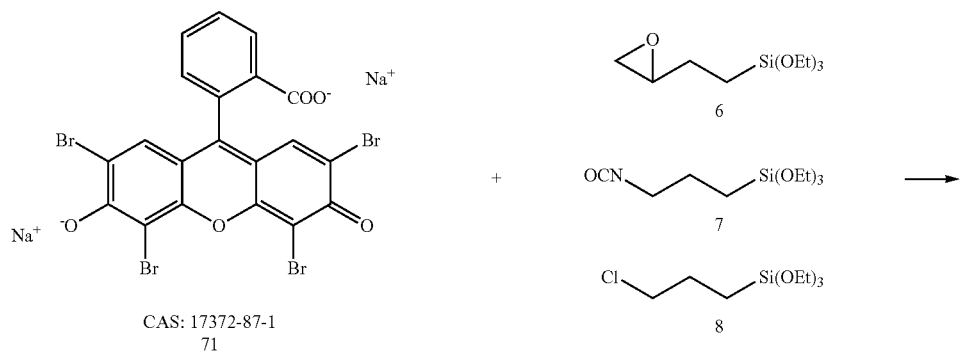

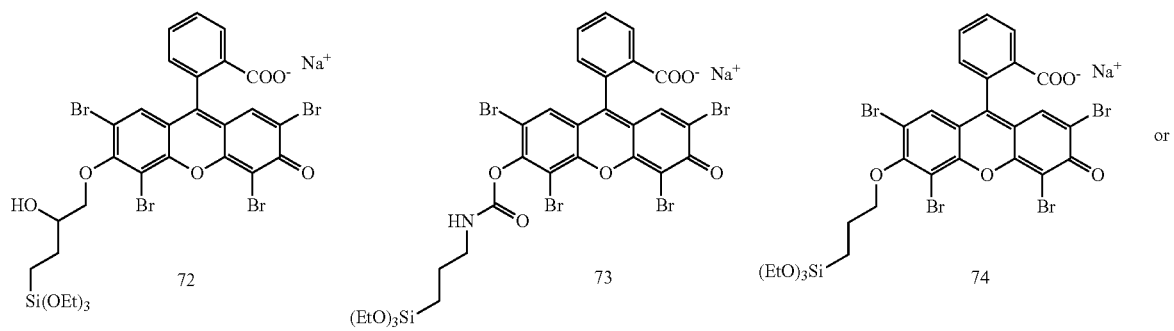

EXAMPLE 13

Phloxine B CAS: 18472-87-2; Φ~0.4-0.6

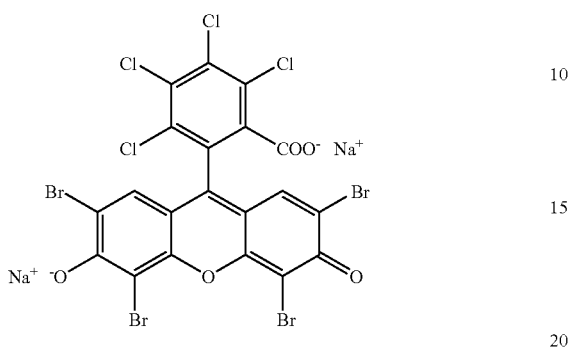

Reaction of substituted Phloxine B Photocatalyst 75 with epoxysilyl ester 6 gives substituted Phloxine B Photocatalyst Composition 76. Reaction of substituted Phloxine B Photocatalyst 75 with isocyanatosilyl ester 7 gives substituted Phloxine B Photocatalyst Composition 77. Reaction of substituted Phloxine B Photocatalyst 75 with chlorosilyl ester 8 gives substituted Phloxine B Photocatalyst Composition 78.

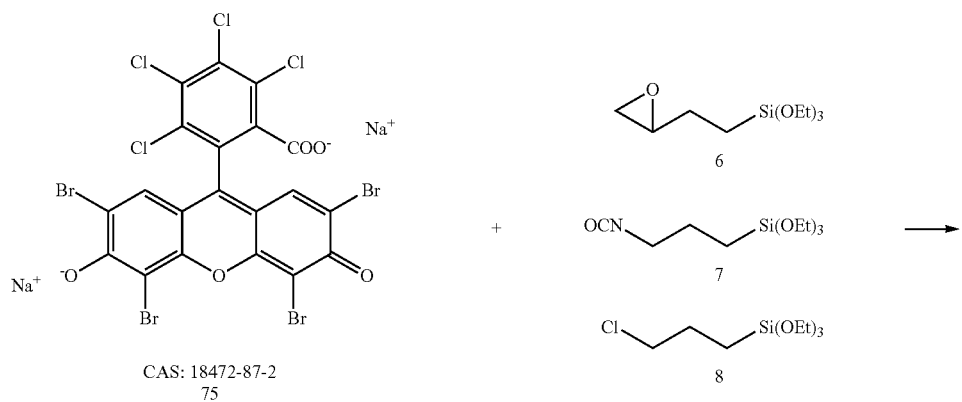

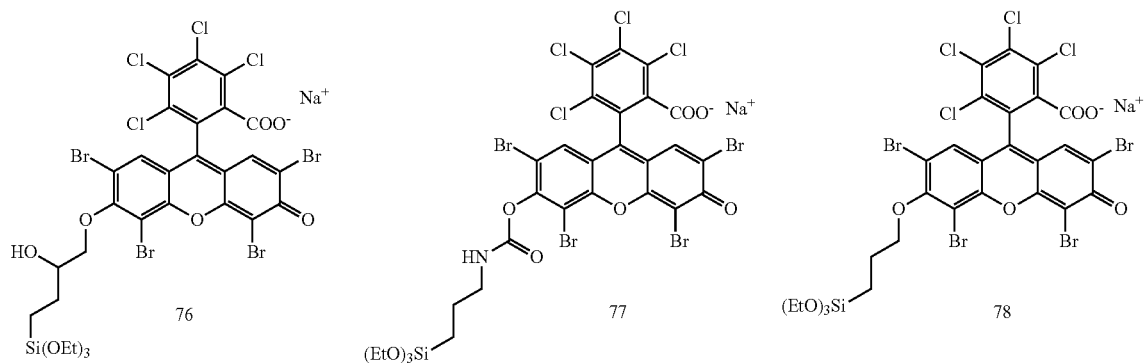

EXAMPLE 14

Rose Bengal DiSodium CAS: 632-69-9; Φ~0.8

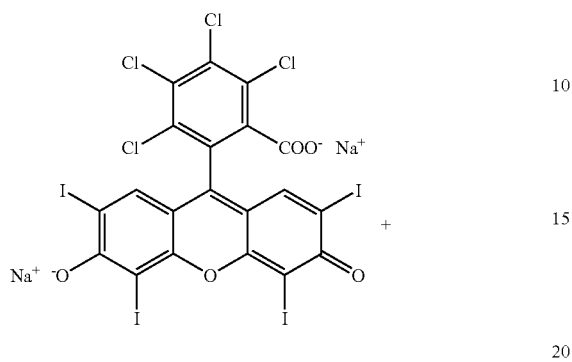

Reaction of substituted Rose Bengal DiSodium Photocatalyst 79 with epoxysilyl ester 6 gives substituted Rose Bengal DiSodium Photocatalyst Composition 80. Reaction of substituted Rose Bengal DiSodium Photocatalyst 79 with isocyanatosilyl ester 7 gives substituted Rose Bengal DiSodium Photocatalyst Composition 81. Reaction of substituted Rose Bengal DiSodium Photocatalyst 79 with chlorosilyl ester 8 gives substituted Rose Bengal DiSodium Photocatalyst Composition 82.

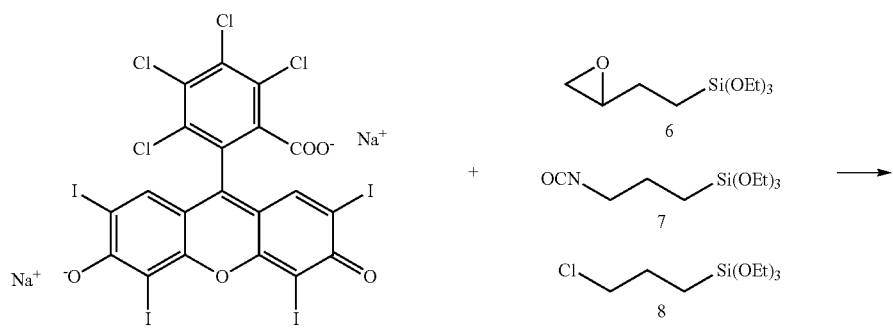

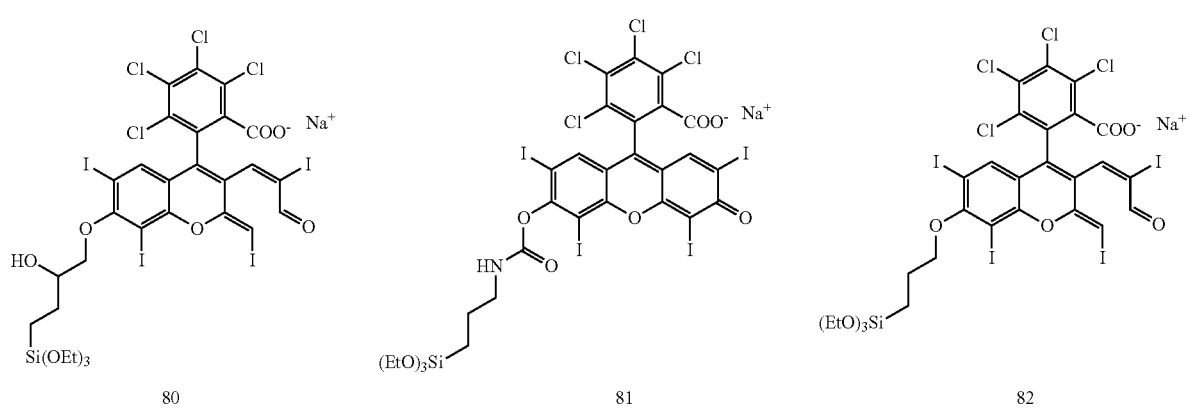

EXAMPLE 15

Erythrosin CAS: 16423-68-0; Φ~0.5-0.6

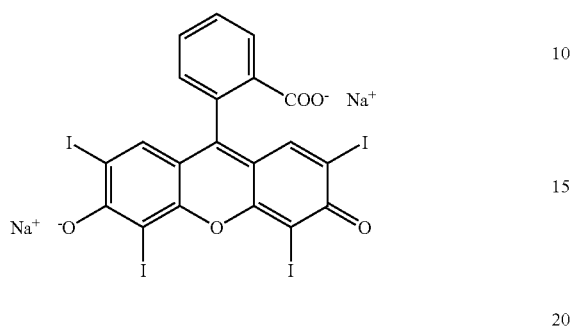

Reaction of substituted Erythrosin Photocatalyst 83 with epoxysilyl ester 6 gives substituted Erythrosin Photocatalyst Composition 84. Reaction of substituted Erythrosin photocatalyst 83 with isocyanatosilyl ester 7 gives substituted Erythrosin Photocatalyst Composition 85. Reaction of substituted Erythrosin Photocatalyst 83 with chlorosilyl ester 8 gives substituted Erythrosin Photocatalyst Composition 86.

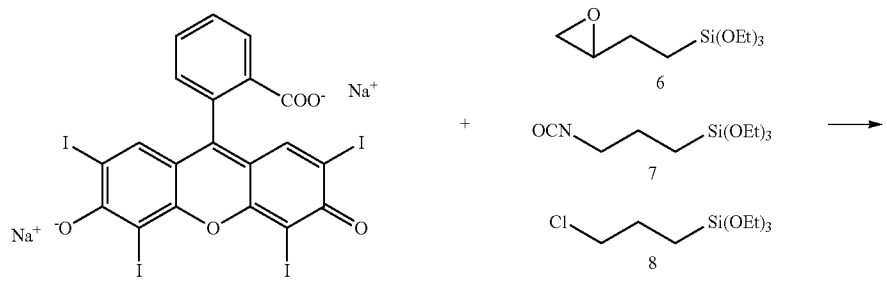

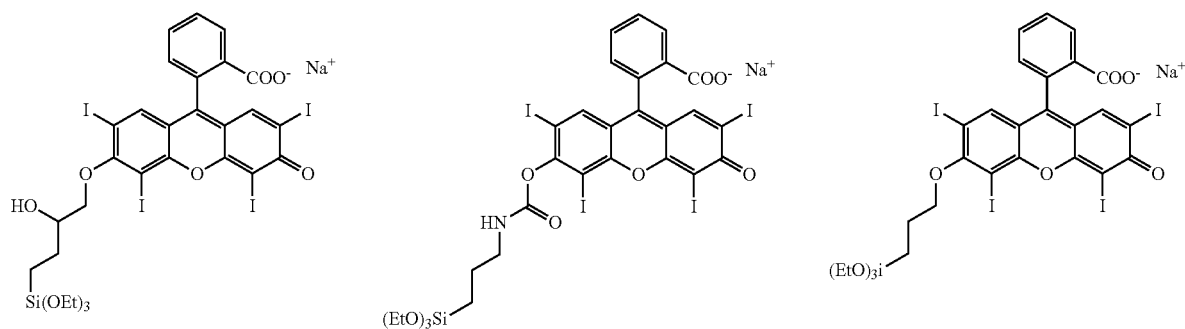

EXAMPLE 16

Naphthalene CAS: 91-20-3; Φ~0.7-1

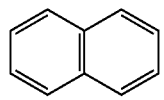

Reaction of substituted Naphthalene Photocatalyst 87 with aminosilyl ester 4 gives substituted Naphthalene Photocatalyst Composition 88. Reaction of substituted Naphthalene Photocatalyst 87 with mercaptosilyl ester 5 gives substituted Naphthalene Photocatalyst Composition 89.

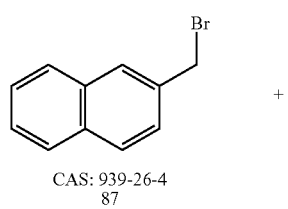

CAS: 939-26-4
87

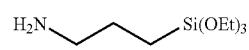
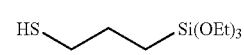

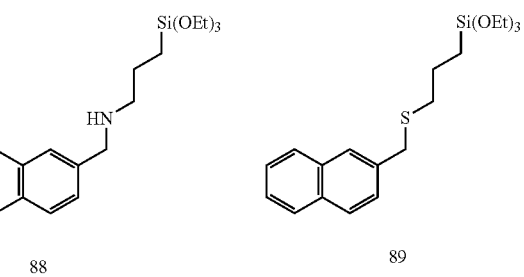

Reaction of substituted Naphthalene Photocatalyst 90A with epoxysilyl ester 6 gives substituted Naphthalene Photocatalyst Composition 91. Reaction of substituted Naphthalene Photocatalyst 90A with isocyanatosilyl ester 7 gives substituted Naphthalene Photocatalyst Composition 92.

Reaction of substituted Naphthalene Photocatalyst 90B with epoxysilyl ester 6 gives substituted Naphthalene Photocatalyst Composition 93. Reaction of substituted Naphthalene Photocatalyst 90B with isocyanatosilyl ester 7 gives substituted Naphthalene Photocatalyst Composition 94.

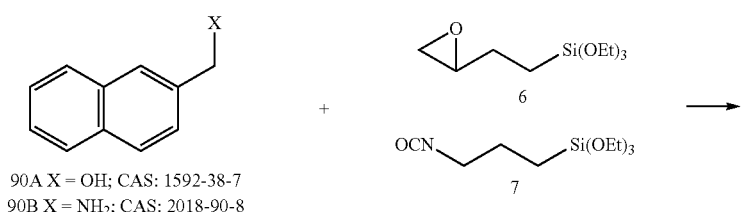

90A X = OH; CAS: 1592-38-7
90B X = NH$_2$; CAS: 2018-90-8

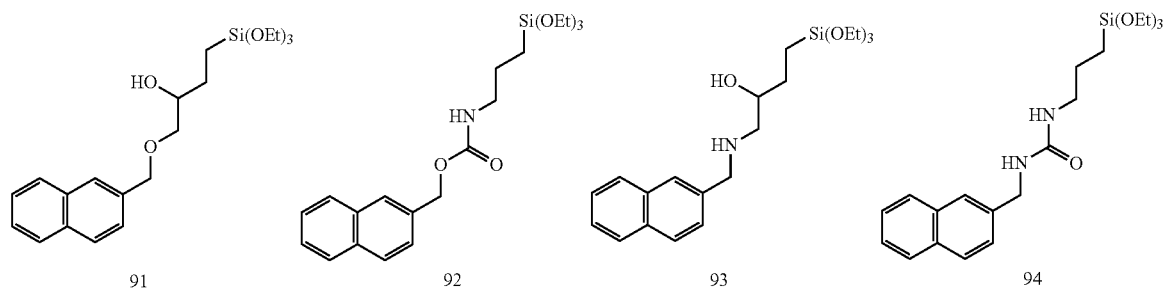

EXAMPLE 17

Phenanthrene CAS: 85-01-8; Φ~0.4-0.6

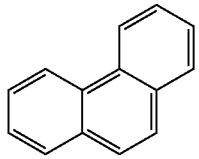 [SMILES: c1ccc2c(c1)ccc1ccccc12]

Reaction of substituted Phenanthrene Photocatalyst 20B with aminosilyl ester 4 gives substituted Phenanthrene Photocatalyst Composition 96. Reaction of substituted Phenanthrene Photocatalyst 20B with mercaptosilyl ester 5 gives substituted Phenanthrene Photocatalyst Composition 97.

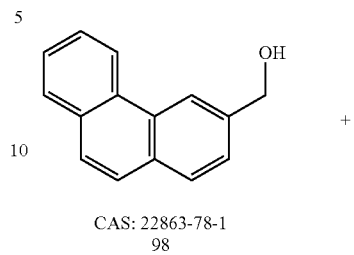

Reaction of substituted Phenanthrene Photocatalyst 98 with epoxysilyl ester 6 gives substituted Phenanthrene Photocatalyst Composition 99. Reaction of substituted Phenanthrene photocatalyst 98 with isocyanatosilyl ester 7 gives substituted Phenanthrene Photocatalyst Composition 100. Reaction of substituted Phenanthrene Photocatalyst 98 with chlorosilyl ester 8 gives substituted Phenanthrene Photocatalyst Composition 101.

EXAMPLE 18

Phenazine CAS: 92-82-0; Φ~0.8-0.9

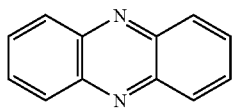

Reaction of substituted Phenazine Photocatalyst 102 with aminosilyl ester 4 gives substituted Phenazine Photocatalyst Composition 103. Reaction of substituted Phenazine Photocatalyst 20B with mercaptosilyl ester 5 gives substituted Phenazine Photocatalyst Composition 104.

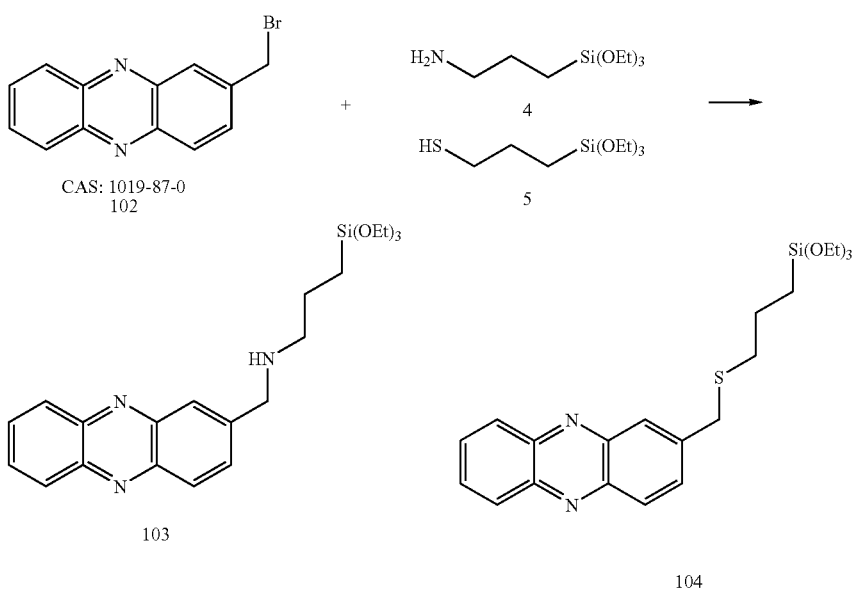

EXAMPLE 19

Thionine CAS: 581-64-6; Φ~0.6

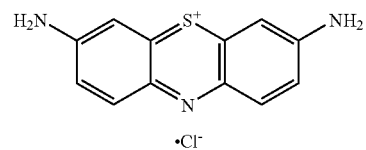 [SMILES: Nc1ccc2nc3ccc(N)cc3[s+]c2c1 ; [Cl-]]

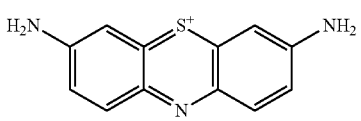

CAS: 581-64-6
105

Reaction of substituted Thionine Photocatalyst 105 with epoxysilyl ester 6 gives substituted Thionine Photocatalyst Composition 106. Reaction of substituted Thionine Photocatalyst 105 with isocyanatosilyl ester 7 gives substituted Thionine Photocatalyst Composition 107. Reaction of substituted Thionine Photocatalyst 105 with chlorosilyl ester 8 gives substituted Thionine Photocatalyst Composition 108.

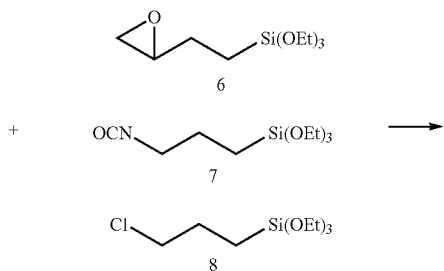

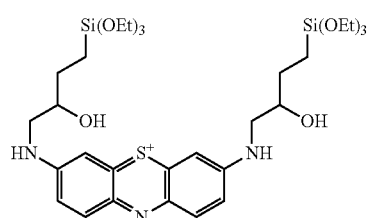

106

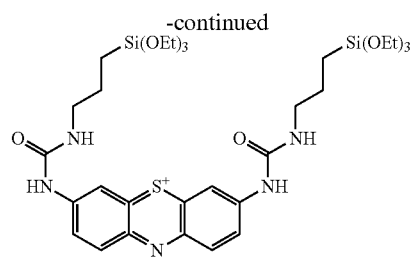

107

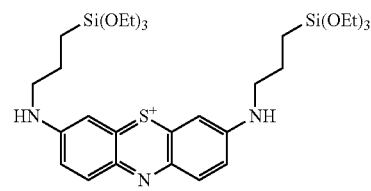

108

EXAMPLE 20

Azure A CAS: 531-53-3; Φ~0.8

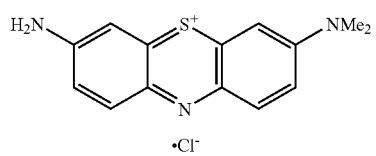 [SMILES: CN(C)c1ccc2nc3ccc(N)cc3[s+]c2c1 ; [Cl-]]

Reaction of substituted Azure A Photocatalyst 109 with epoxysilyl ester 6 gives substituted Azure A Photocatalyst Composition 110. Reaction of substituted Azure A Photocatalyst 109 with isocyanatosilyl ester 7 gives substituted Azure A Photocatalyst Composition 111. Reaction of substituted Azure A Photocatalyst 109 with chlorosilyl ester 8 gives substituted Azure A Photocatalyst Composition 112.

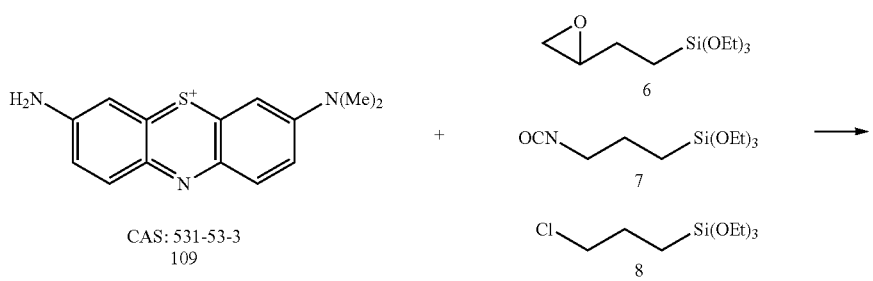

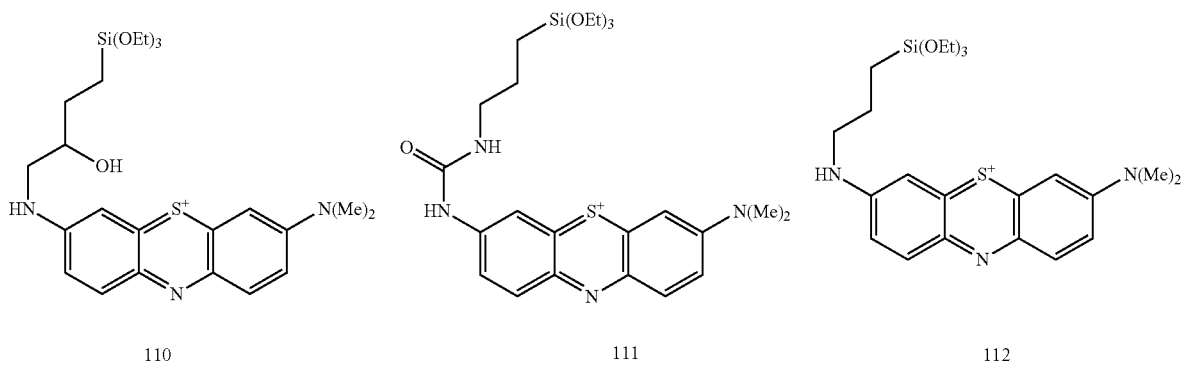

EXAMPLE 21

Azure C CAS: 531-57-7; Φ~0.71 relative to MB

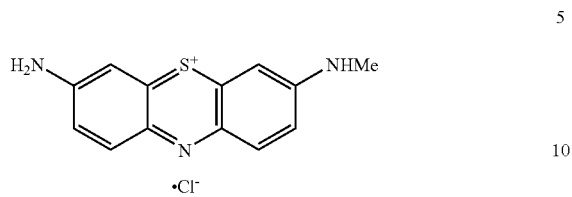

Reaction of substituted Azure C Photocatalyst 113 with epoxysilyl ester 6 gives substituted Azure C Photocatalyst Composition 114. Reaction of substituted Azure C Photocatalyst 113 with isocyanatosilyl ester 7 gives substituted Azure C Photocatalyst Composition 115. Reaction of substituted Azure C Photocatalyst 113 with chlorosilyl ester 8 gives substituted Azure C Photocatalyst Composition 116.

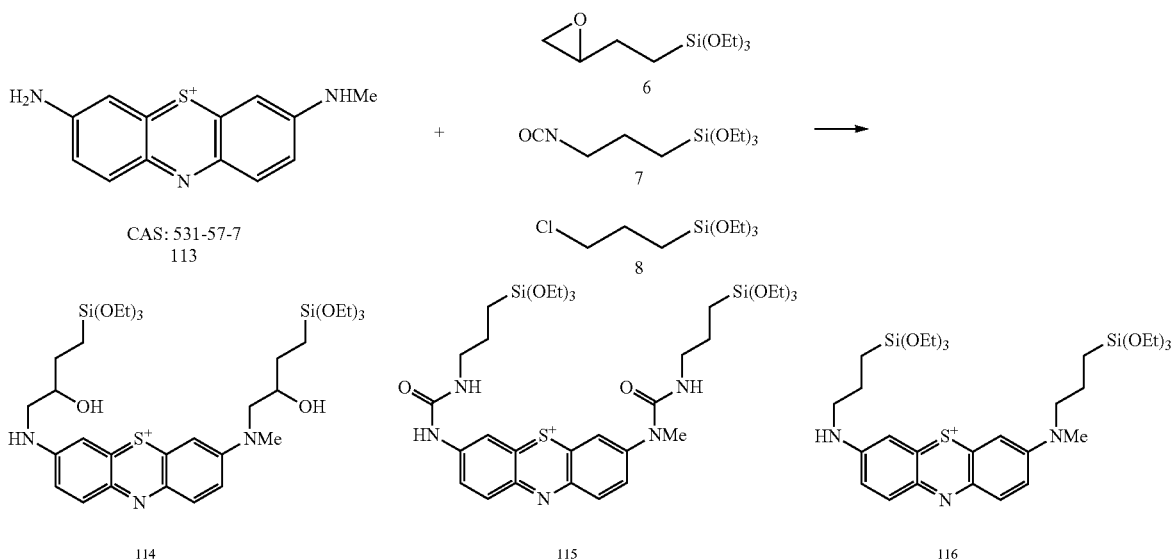

EXAMPLE 22

Toluidine Blue CAS: 92-31-9; Φ~0.8

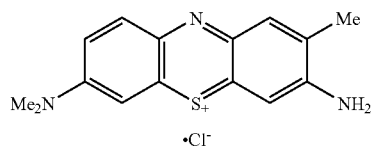 [SMILES: Cc1cc2nc3ccc(N(C)C)cc3[s+]c2cc1N ; [Cl-]]

Reaction of substituted Toluidine Blue Photocatalyst 117 with epoxysilyl ester 6 gives substituted Toluidine Blue Photocatalyst Composition 118. Reaction of substituted Toluidine Blue Photocatalyst 117 with isocyanatosilyl ester 7 gives substituted Toluidine Blue Photocatalyst Composition 119. Reaction of substituted Toluidine Blue Photocatalyst 117 with chlorosilyl ester 8 gives substituted Toluidine Blue Photocatalyst Composition 120.

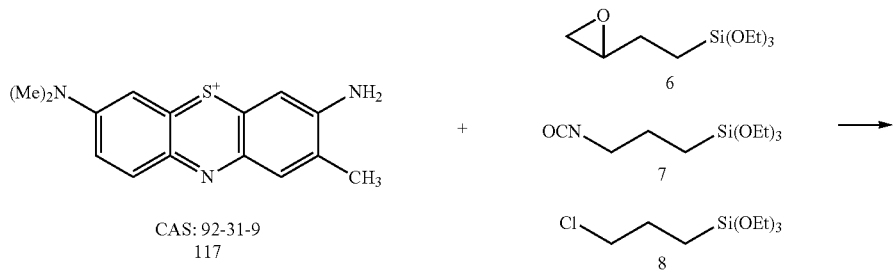

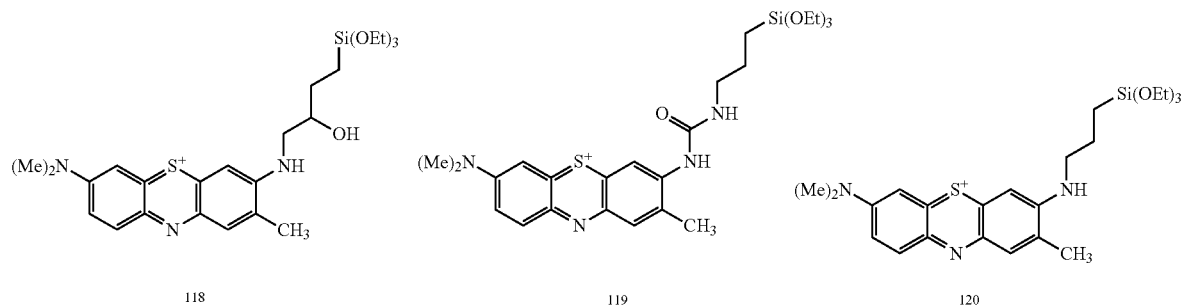

118   119   120

EXAMPLE 23

New Methylene Blue CAS: 1934-16-3; Φ~1.35

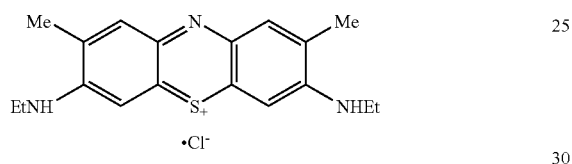

Reaction of substituted New Methylene Blue Photocatalyst 121 with epoxysilyl ester 6 gives substituted New Methylene Blue Photocatalyst Composition 122. Reaction of substituted New Methylene Blue photocatalyst 121 with isocyanatosilyl ester 7 gives substituted New Methylene Blue Photocatalyst Composition 123. Reaction of substituted New Methylene Blue Photocatalyst 121 with chlorosilyl ester 8 gives substituted New Methylene Blue Photocatalyst Composition 124.

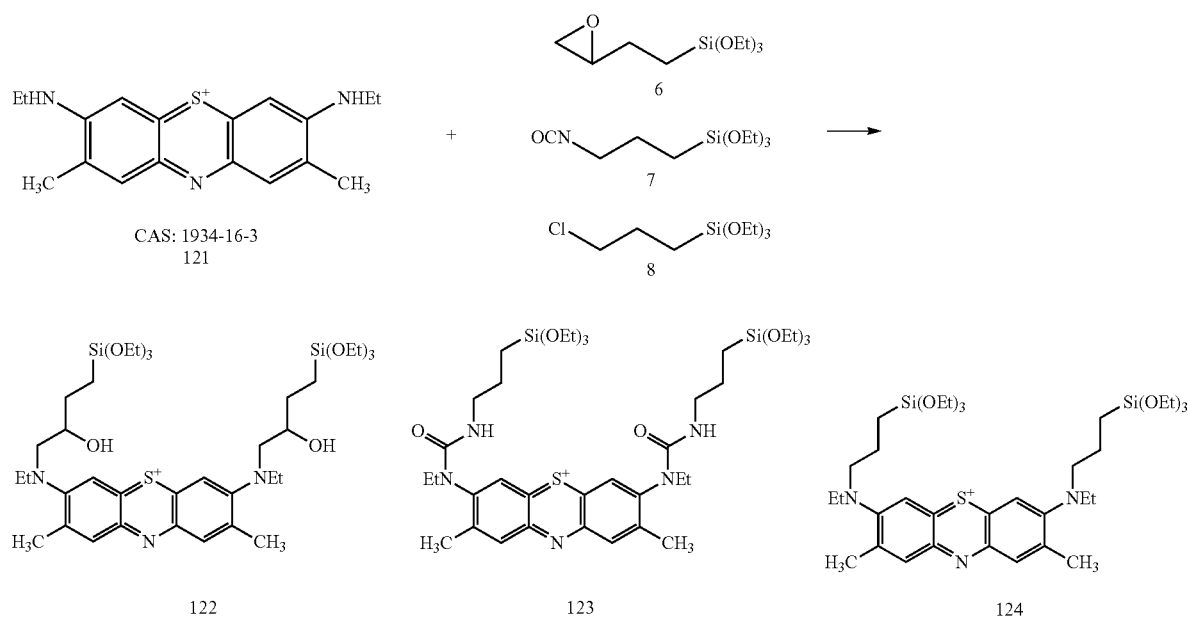

EXAMPLE 24

Pyrene CAS: 129-00-0; Φ~0.8

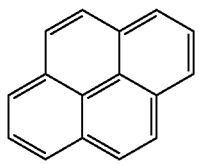 [SMILES: c1cc2ccc3cccc4ccc(c1)c2c34]

Reaction of substituted Pyrene Photocatalyst 125 with aminosilyl ester 4 gives substituted Pyrene Photocatalyst Composition 126. Reaction of substituted Pyrene Photocatalyst 125 with mercaptosilyl ester 5 gives substituted Pyrene Photocatalyst Composition 127.

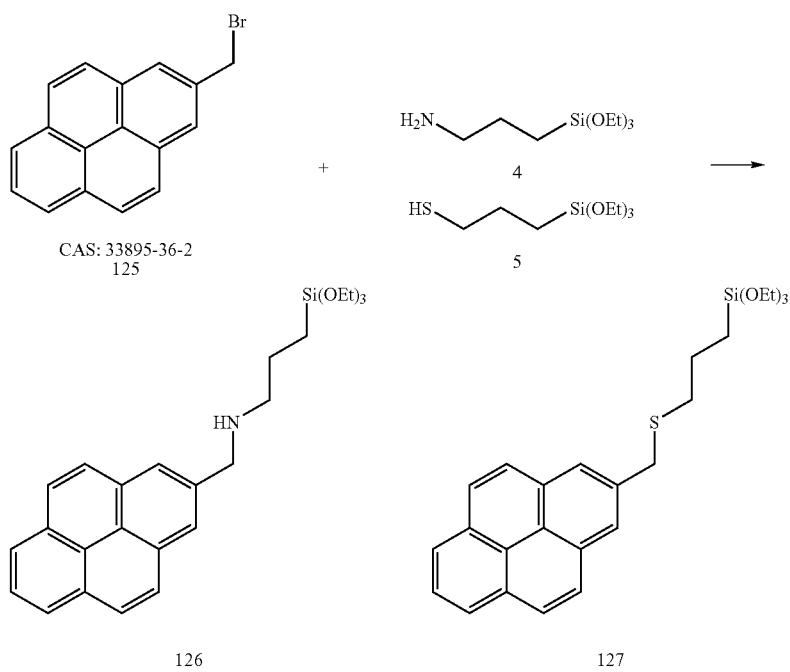

Reaction of substituted Pyrene Photocatalyst 128 with epoxysilyl ester 6 gives substituted Pyrene Photocatalyst Composition 129. Reaction of substituted Pyrene Photocatalyst 128 with isocyanatosilyl ester 7 gives substituted Pyrene Photocatalyst Composition 130. Reaction of substituted Pyrene Photocatalyst 128 with chlorosilyl ester 8 gives P substituted Pyrene hotocatalyst Composition 131.

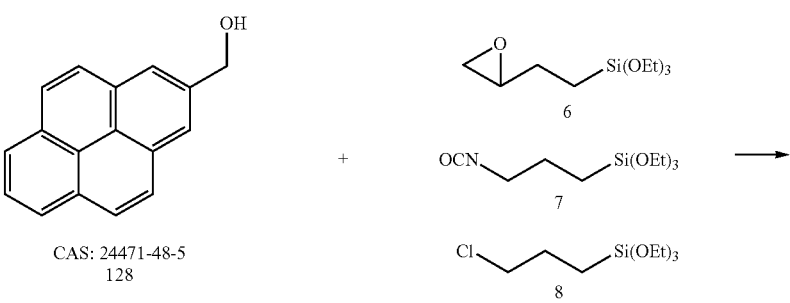

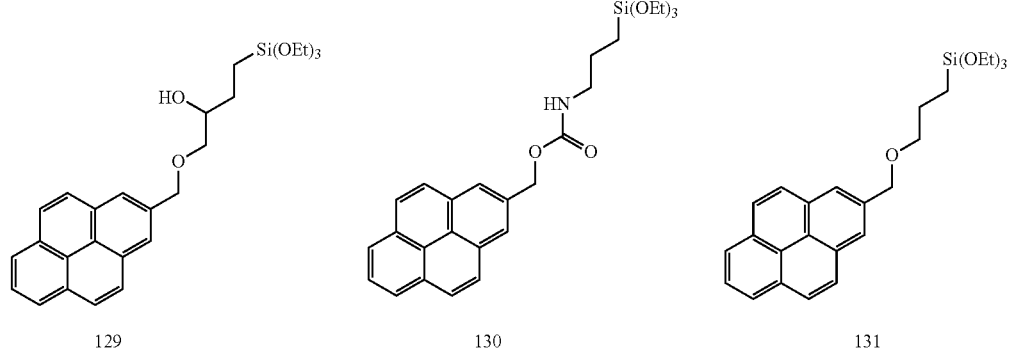

129  130  131

EXAMPLE 25

Quinoxaline CAS: 91-19-0; Φ~0.91

Reaction of substituted Quinoxaline Photocatalyst 132 with aminosilyl ester 4 gives substituted Quinoxaline Photocatalyst Composition 133. Reaction of substituted Quinoxaline photocatalyst 132 with mercaptosilyl ester 5 gives Photocatalyst Composition 134.

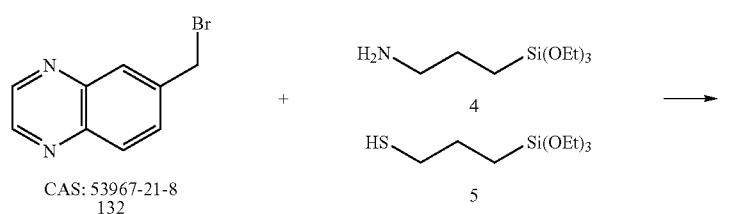

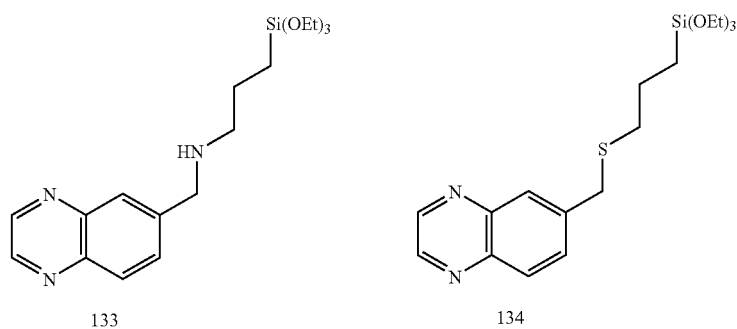

Reaction of substituted Quinoxaline photocatalyst 135 with epoxysilyl ester 6 gives substituted Quinoxaline Photocatalyst Composition 136. Reaction of substituted Quinoxaline photocatalyst 135 with isocyanatosilyl ester 7 gives substituted Quinoxaline Photocatalyst Composition 137. Reaction of substituted Quinoxaline photocatalyst 135 with chlorosilyl ester 8 gives substituted Quinoxaline Photocatalyst Composition 138.

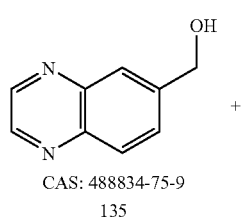

CAS: 488834-75-9
135

+

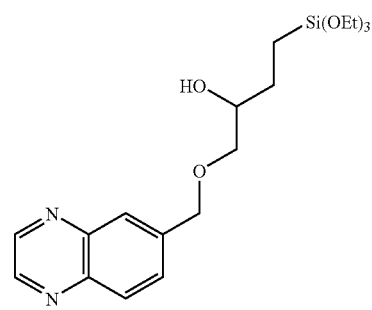

6

7

8

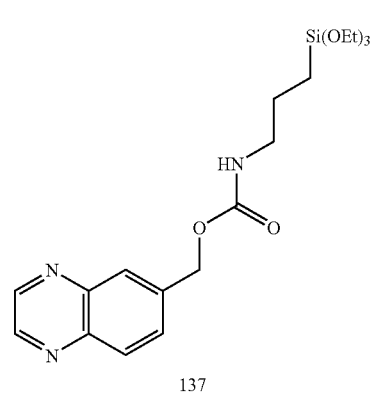

136

137

138

EXAMPLE 26

Retinol CAS: 68-26-8; Φ~0.7

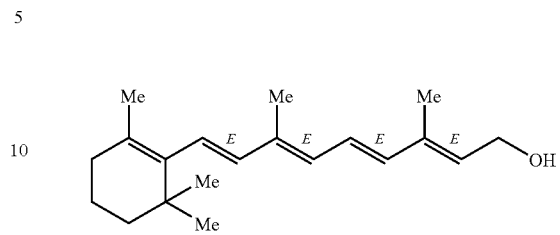

Reaction of substituted Retinol Photocatalyst 139 with epoxysilyl ester 6 gives substituted Retinol Photocatalyst Composition 140. Reaction of substituted Retinol photocatalyst 139 with isocyanatosilyl ester 7 gives substituted Retinol Photocatalyst Composition 141. Reaction of substituted Retinol photocatalyst 139 with chlorosilyl ester 8 gives substituted Retinol Photocatalyst Composition 142.

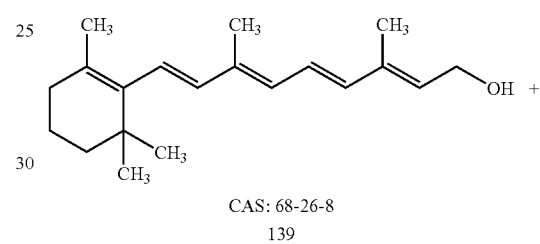

CAS: 68-26-8
139

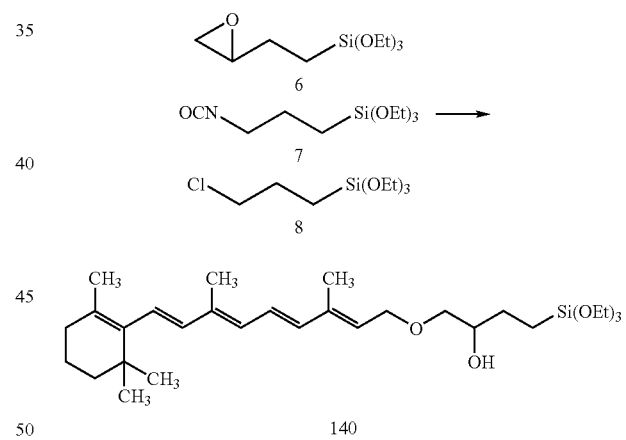

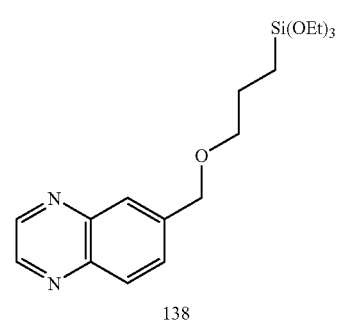

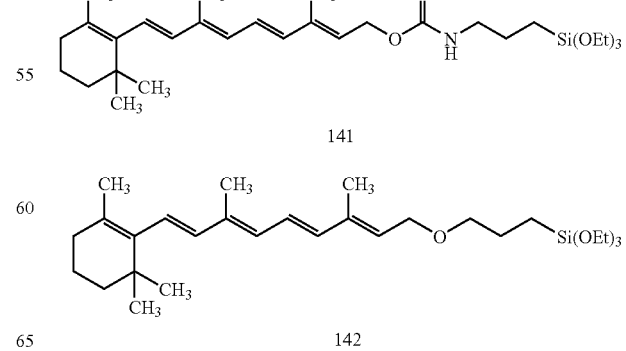

140

141

142

EXAMPLE 27

Riboflavin (Vitamin B2) CAS: 83-88-5; Φ~0.5

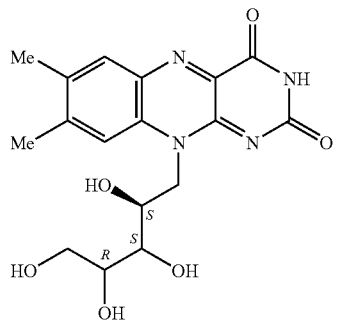

Reaction of substituted Riboflavin Photocatalyst 143 with epoxysilyl ester 6 gives substituted Riboflavin Photocatalyst Composition 144. Reaction of substituted Riboflavin photocatalyst 143 with isocyanatosilyl ester 7 gives substituted Riboflavin Photocatalyst Composition 145. Reaction of substituted Riboflavin photocatalyst 143 with chlorosilyl ester 8 gives substituted Riboflavin Photocatalyst Composition 146.

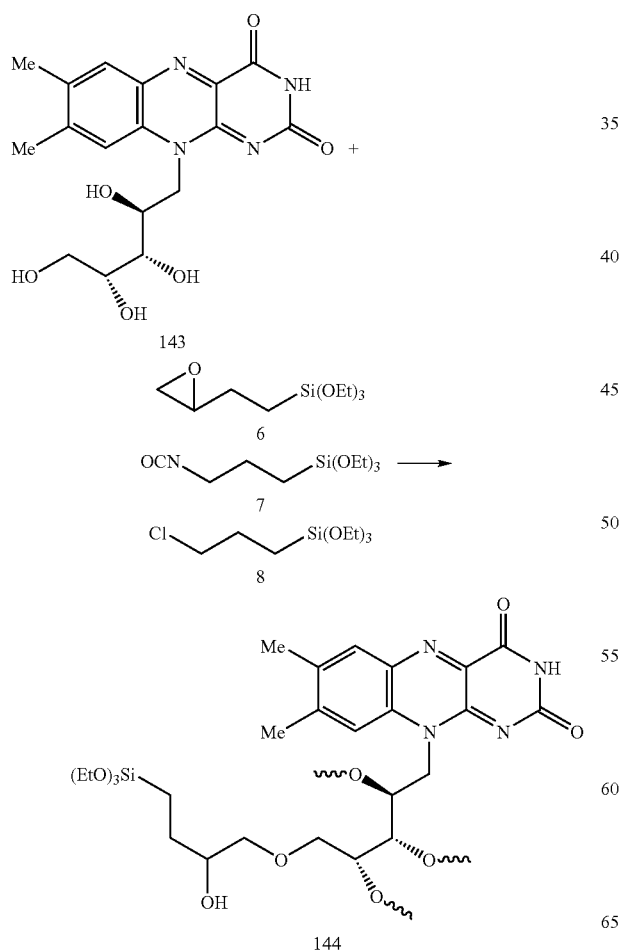

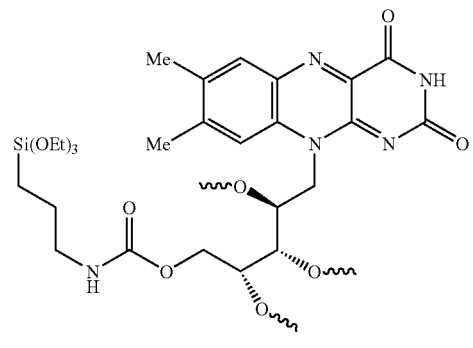

145

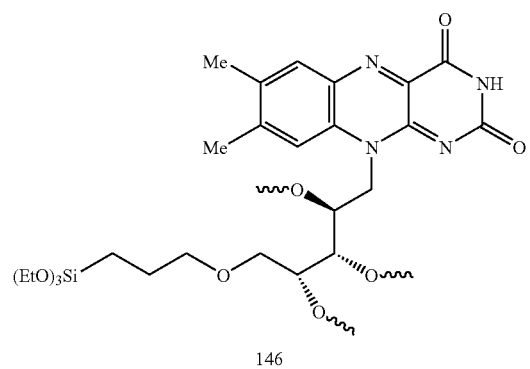

146

EXAMPLE 28

Rubrene CAS: 517-51-1; Φ~1

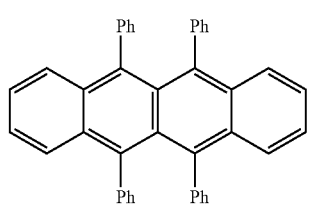 [SMILES: c1ccc(-c2c3ccccc3c(-c3ccccc3)c3c(-c4ccccc4)c4ccccc4c(-c4ccccc4)c23)cc1]

Reaction of substituted Rubrene Photocatalyst 147 with epoxysilyl ester 6 gives substituted Rubrene Photocatalyst Composition 148. Reaction of substituted Rubrene photocatalyst 147 with isocyanatosilyl ester 7 gives substituted Rubrene Photocatalyst Composition 149. Reaction of substituted Rubrene photocatalyst 147 with chlorosilyl ester 8 gives substituted Rubrene Photocatalyst Composition 150.

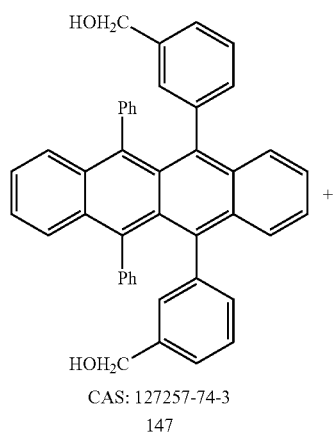
CAS: 127257-74-3
147
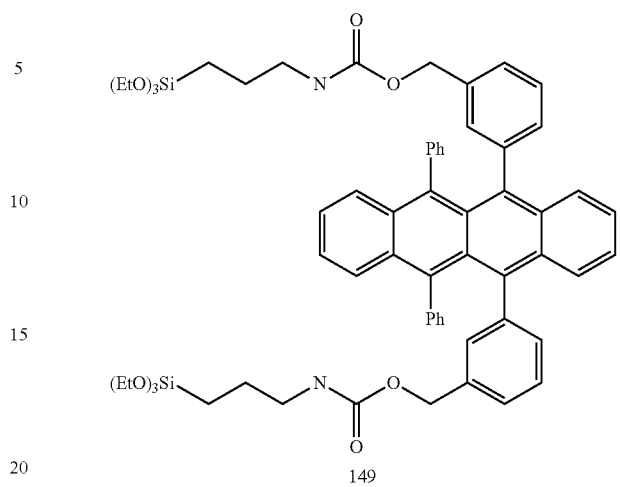
149
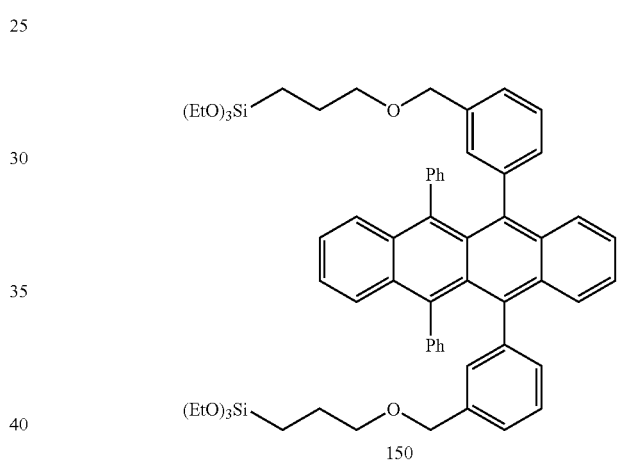
150
EXAMPLE 29
p-Terphenyl CAS: 92-94-4; Φ~0.9
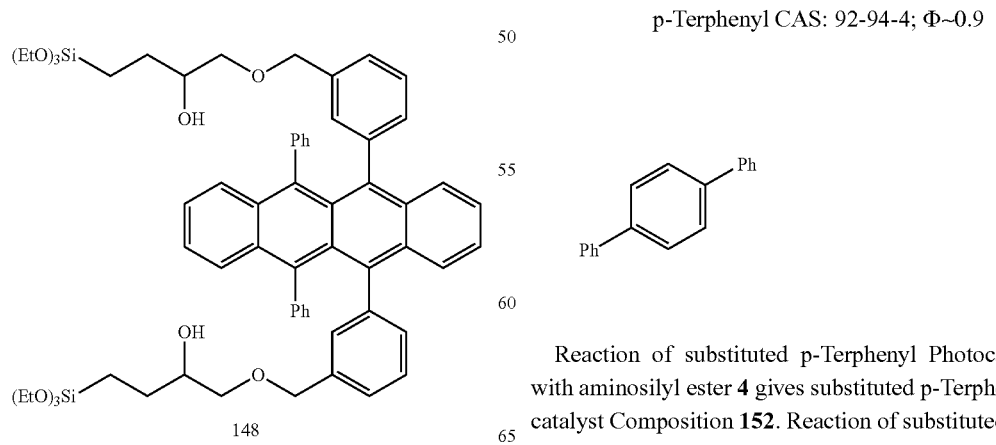
148
Reaction of substituted p-Terphenyl Photocatalyst 151 with aminosilyl ester 4 gives substituted p-Terphenyl Photocatalyst Composition 152. Reaction of substituted p-Terphenyl Photocatalyst 151 with mercaptosilyl ester 5 gives substituted p-Terphenyl Photocatalyst Composition 153.

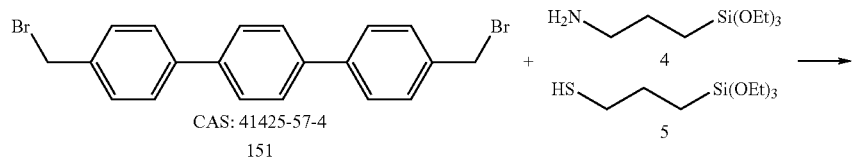
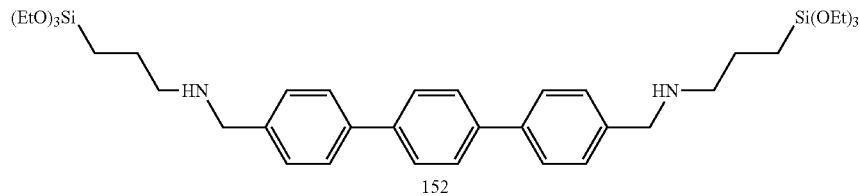
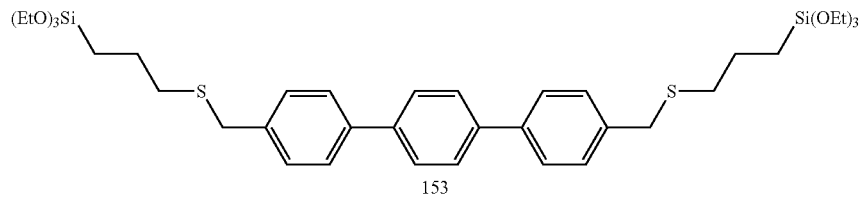
EXAMPLE 30
Bacteriochlorophyll A CAS: 17499-98-8; Φ~0.4
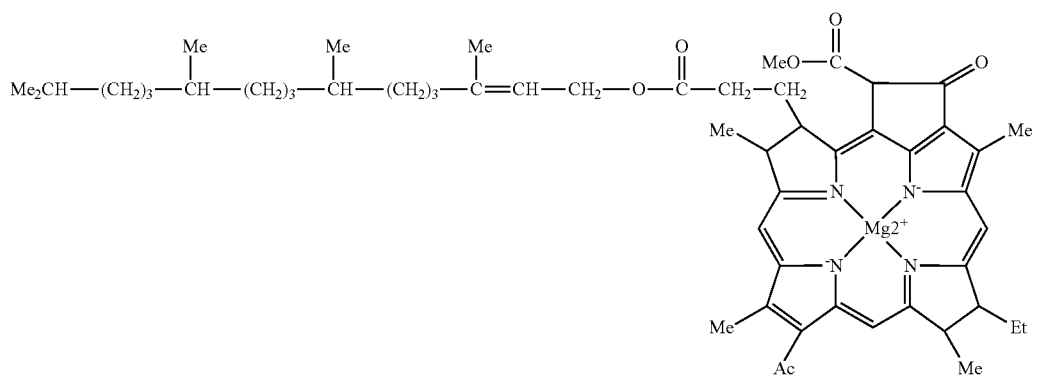
Reaction of substituted Bacteriochlorophyll A Photocatalyst 154 with aminosilyl ester 4 gives Bacteriochlorophyll A Photocatalyst Composition 155.
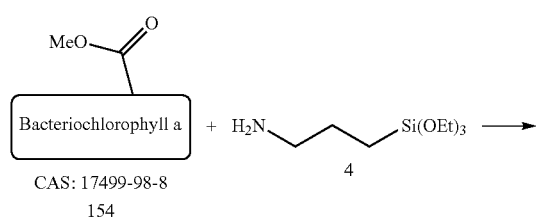
-continued
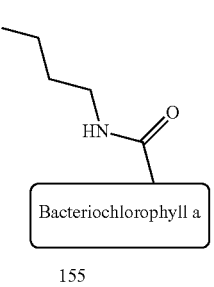

EXAMPLE 31
Bacteriochlorophyll B CAS: 53199-29-4; Φ~0.5
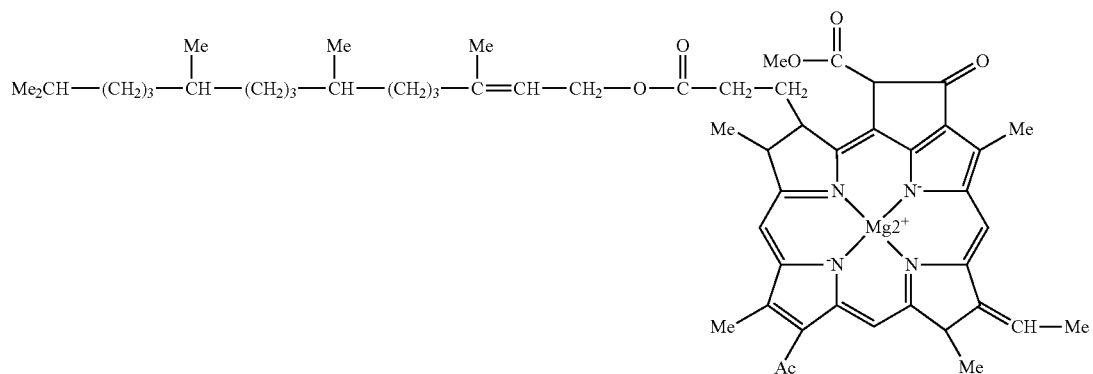
Reaction of substituted Bacteriochlorophyll B Photocatalyst 156 with aminosilyl ester 4 gives Bacteriochlorophyll B Photocatalyst Composition 157.
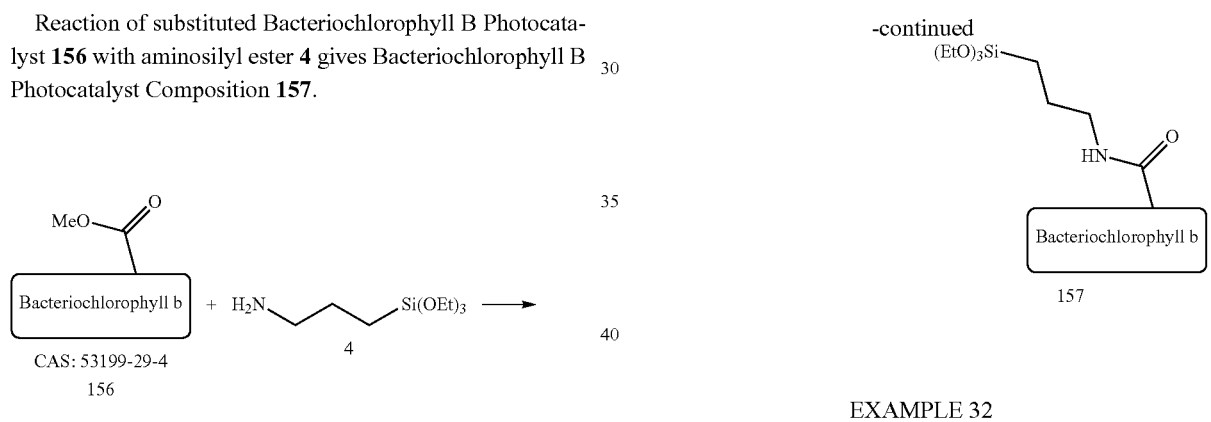
EXAMPLE 32
Chlorophyll A CAS: 479-61-8; Φ~0.5-0.7
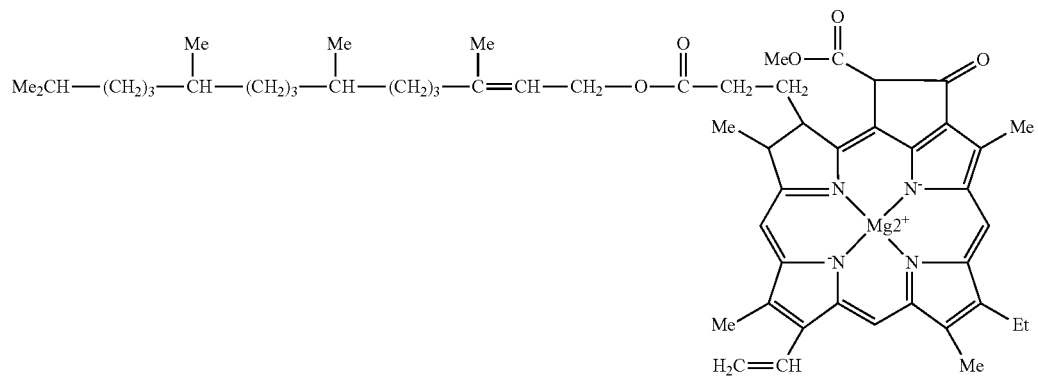

Reaction of substituted Chlorophyll A Photocatalyst 158 with aminosilyl ester 4 gives substituted Chlorophyll A Photocatalyst Composition 159.
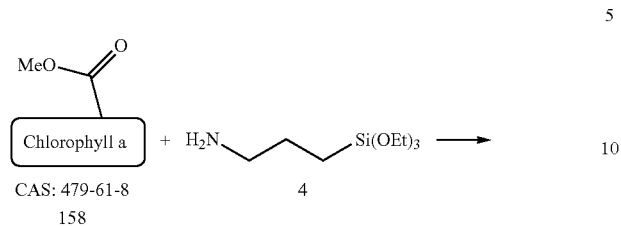
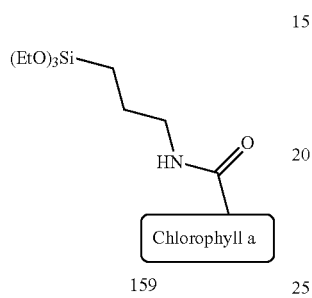
EXAMPLE 33
Chlorophyll B CAS: 519-62-0; Φ~0.7-0.8
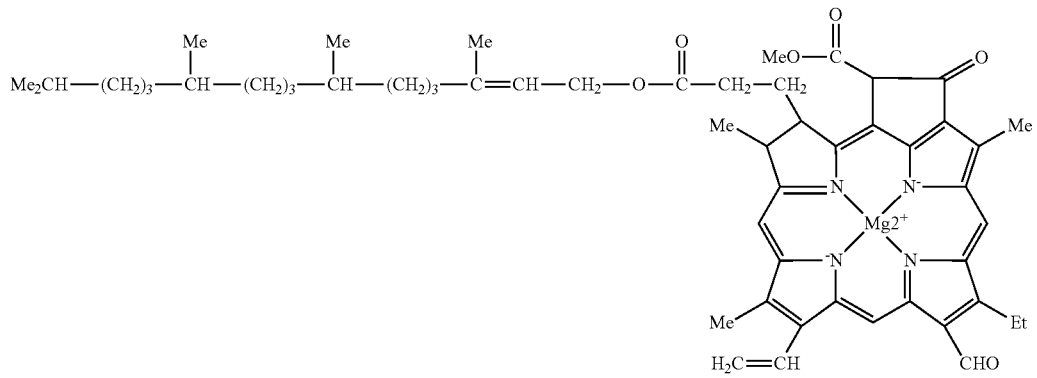
Reaction of substituted Chlorophyll B photocatalyst 160 with aminosilyl ester 4 gives substituted Chlorophyll B Photocatalyst Composition 161.
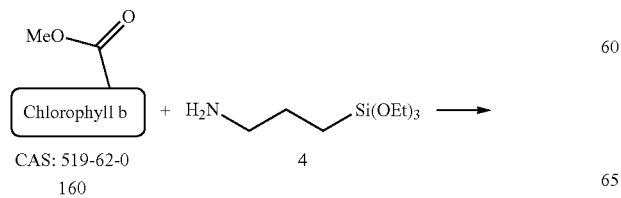
-continued
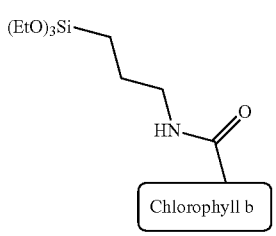

EXAMPLE 34
Pheophytin A CAS: 603-17-8; Φ~0.6-0.7
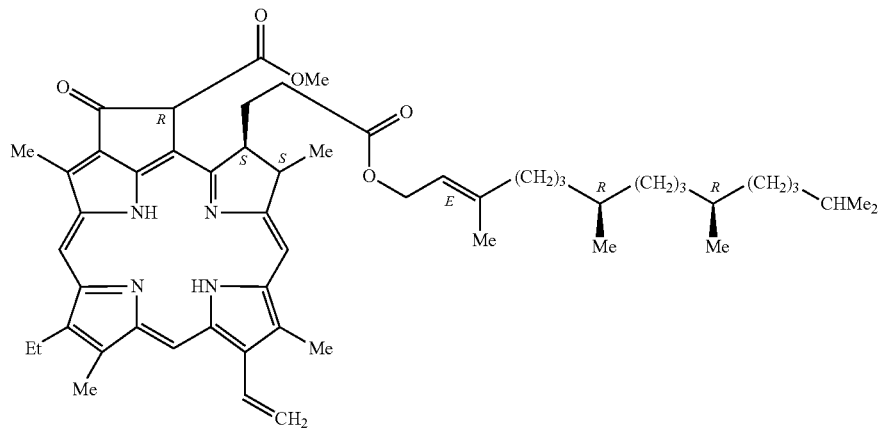
Reaction of substituted Pheophytin A Photocatalyst 162 with aminosilyl ester 4 gives substituted Pheophytin A Photocatalyst Composition 163.
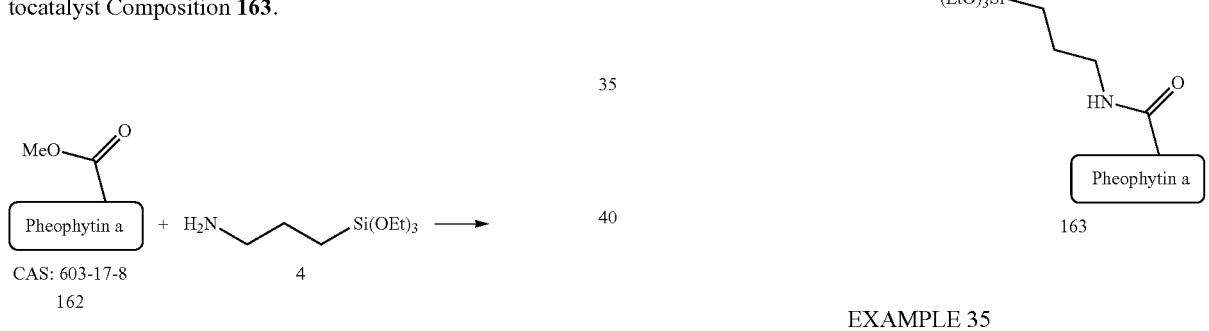
-continued
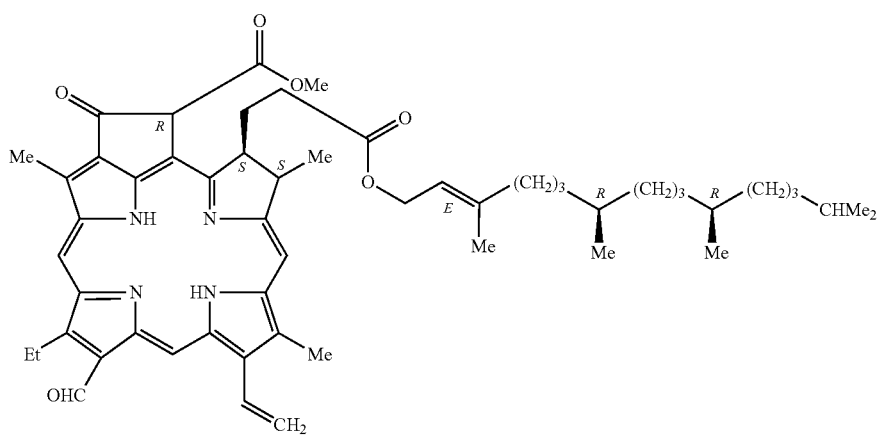
163
EXAMPLE 35
Pheophytin B CAS: 3147-18-0; Φ~0.7-0.8~

Reaction of substituted Pheophytin B Photocatalyst 164 with aminosilyl ester 4 gives substituted Pheophytin B Photocatalyst Composition 165.

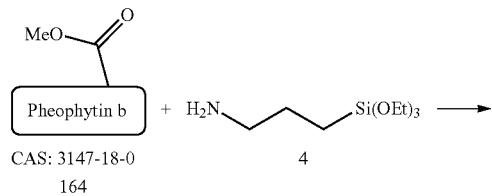

CAS: 3147-18-0
164

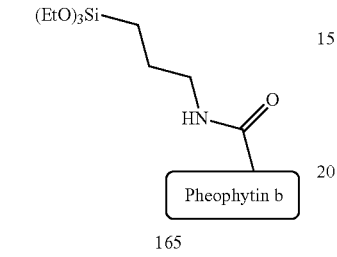

165

EXAMPLE 36

Pheophorbide A CAS: 15664-29-6; Φ~0.4-0.7

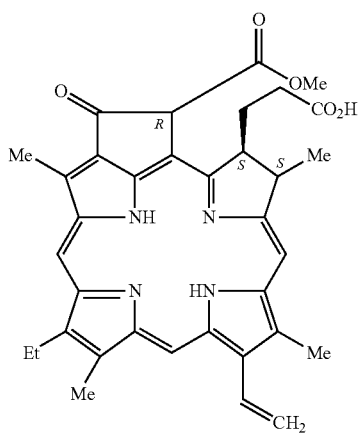

Reaction of substituted Pheophorbide A Photocatalyst 166 with aminosilyl ester 4 gives substituted Pheophorbide A Photocatalyst Composition 167.

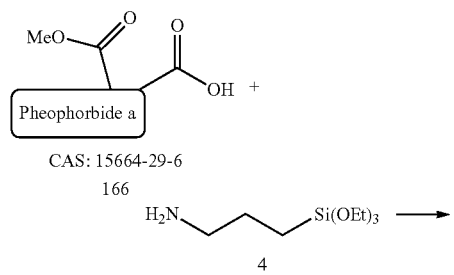

CAS: 15664-29-6
166

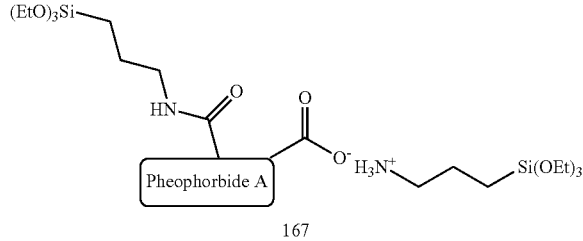

167

EXAMPLE 37

Protochlorophyllide CAS: 20369-67-9; Φ~0.7-0.8

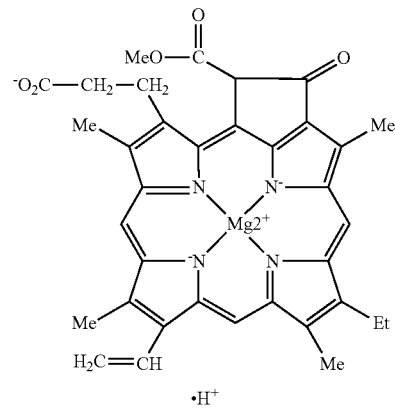

Reaction of substituted Protochlorophyllide photocatalyst 168 with aminosilyl ester 4 gives substituted Protochlorophyllide Photocatalyst Composition 169.

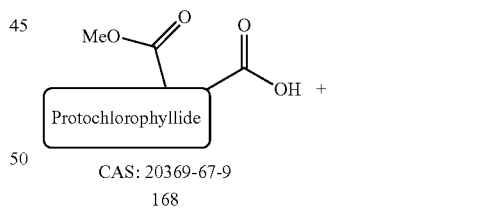

CAS: 20369-67-9
168

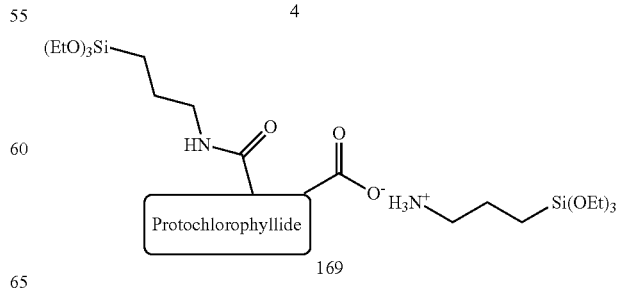

169

EXAMPLE 38

Protochlorophyll CAS: 14751-08-7; Φ~0.6-0.8

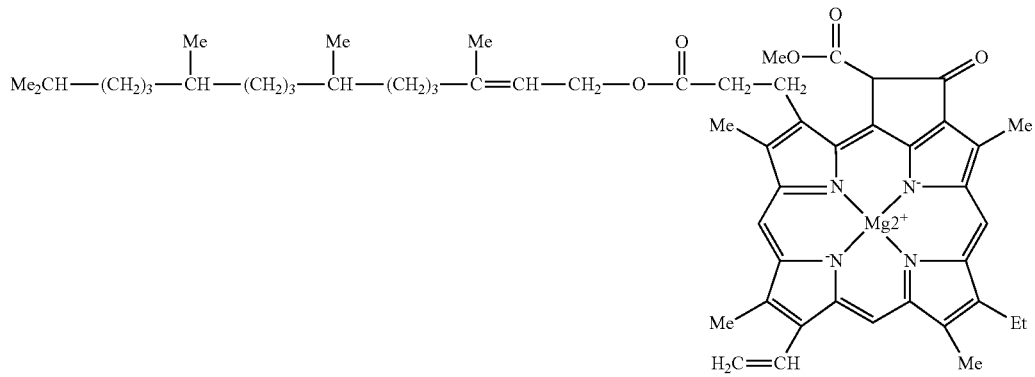

Reaction of substituted Protochlorophyll Photocatalyst 170 with aminosilyl ester 4 gives substituted Protochlorophyll Photocatalyst Composition 171.

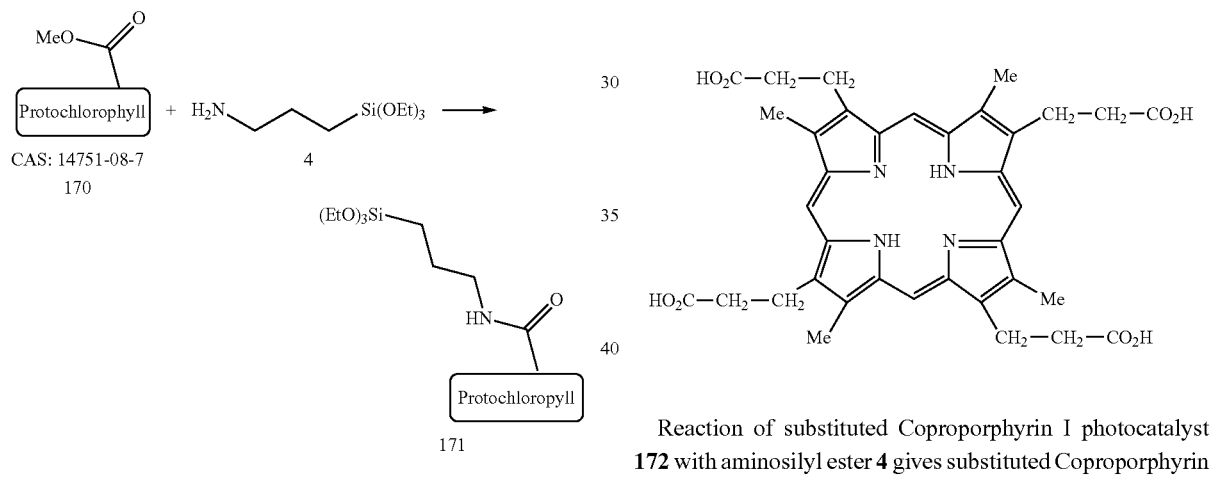

EXAMPLE 39

Coproporphyrin I CAS: 531-14-6; Φ~0.6

Reaction of substituted Coproporphyrin I photocatalyst 172 with aminosilyl ester 4 gives substituted Coproporphyrin I Photocatalyst Composition 173.

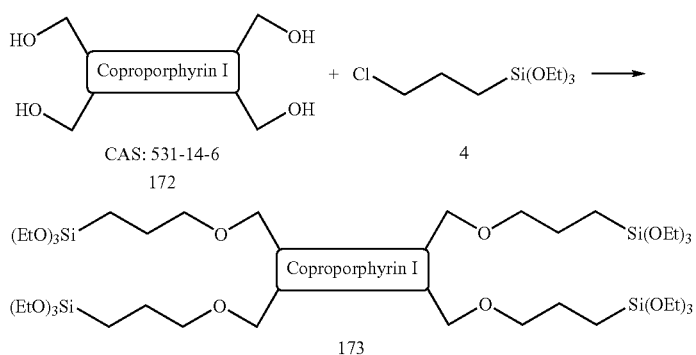

EXAMPLE 40

Fullerene-$C_{60}$ CAS: 99685-96-8; Φ~1

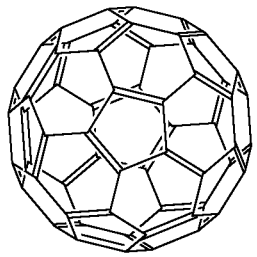 [SMILES: c12c3c4c5c1c1c6c7c2c2c8c3c3c9c4c4c%10c5c5c1c1c6c6c%11c7c2c2c7c8c3c3c8c9c4c4c9c%10c5c5c1c1c6c6c%11c2c2c7c3c3c8c4c4c9c5c1c1c6c2c3c41]

Reaction of substituted Fullerene-$C_{60}$ Photocatalyst 174 with aminosilyl ester 4 gives substituted Fullerene-$C_{60}$ Photocatalyst Composition 175.

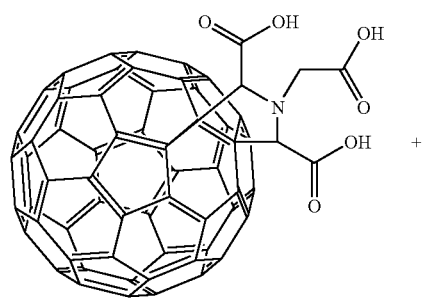

C60 Pyrrolidine tris-acid
174

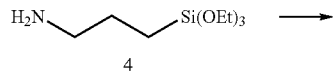

4

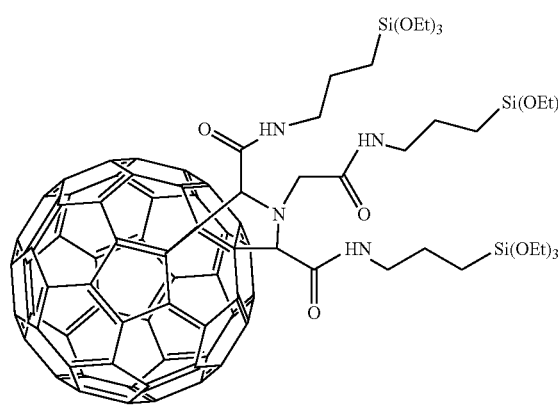

175

Reaction of substituted Fullerene-$C_{60}$ Photocatalyst 176 with chlorosilyl ester 8 gives substituted Fullerene-$C_{60}$ Photocatalyst Composition 177.

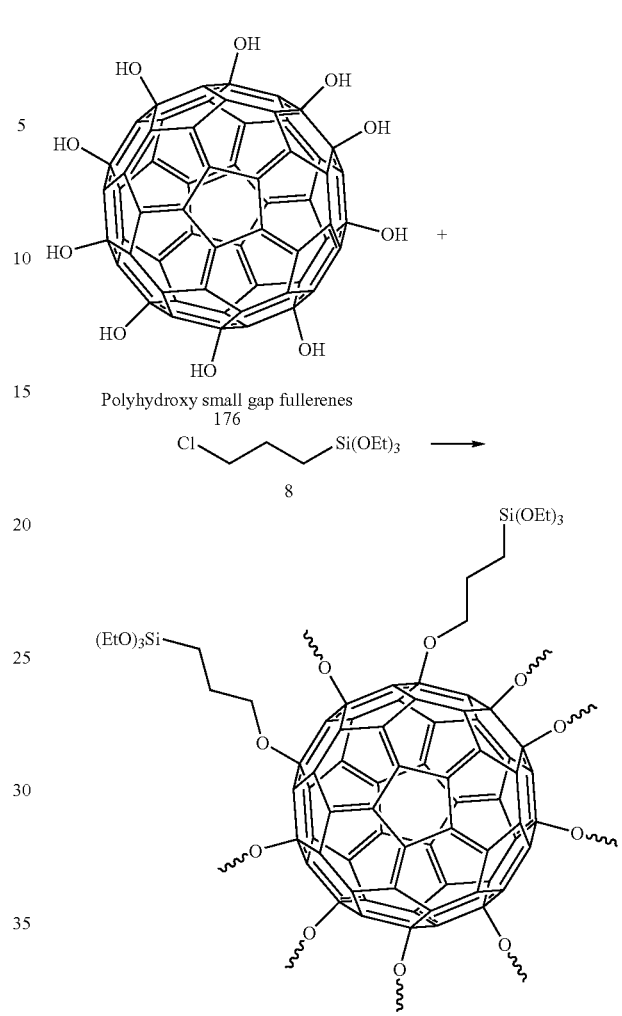

Polyhydroxy small gap fullerenes
176

177

Reaction of substituted Fullerene-$C_{60}$ Photocatalyst 178 with aminosilyl ester 4 gives substituted Fullerene-$C_{60}$ Photocatalyst Composition 179.

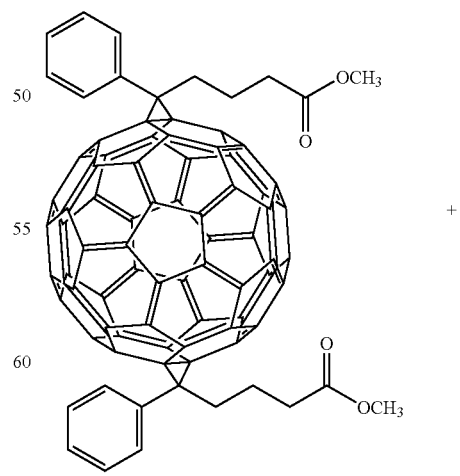

Diphenyl C62 bis(butyric acid methyl ester)
178

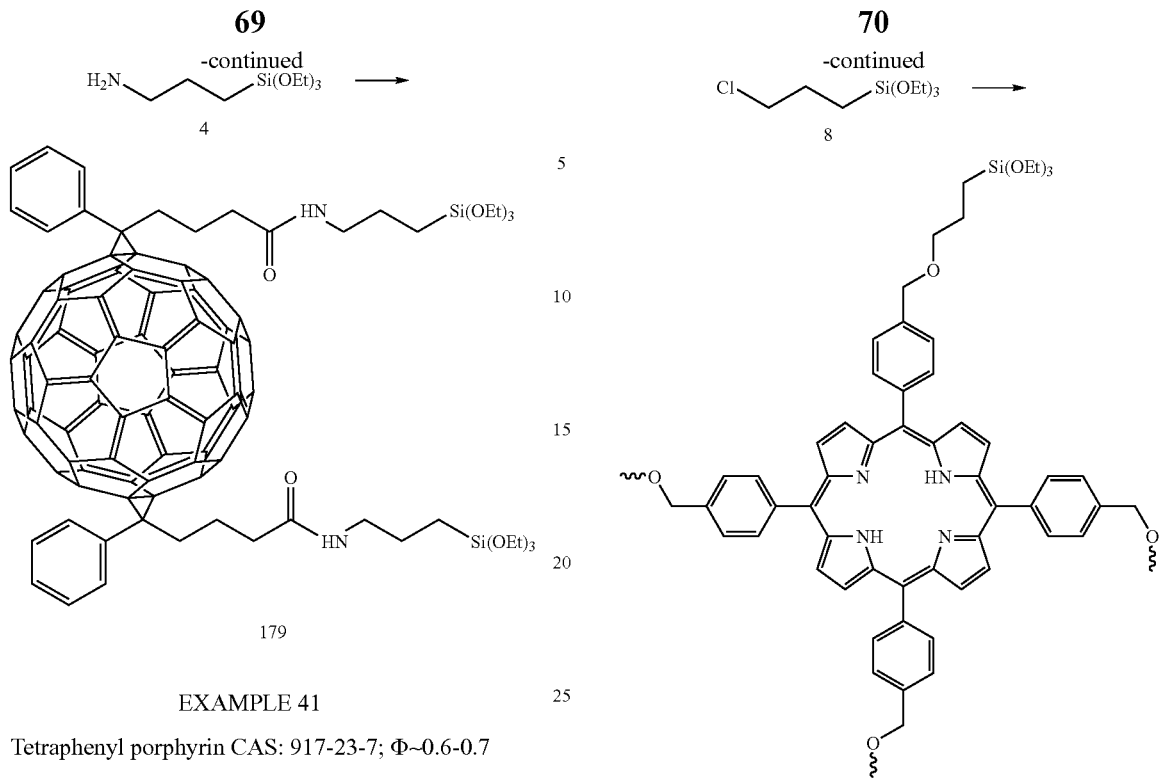

EXAMPLE 41

Tetraphenyl porphyrin CAS: 917-23-7; Φ~0.6-0.7

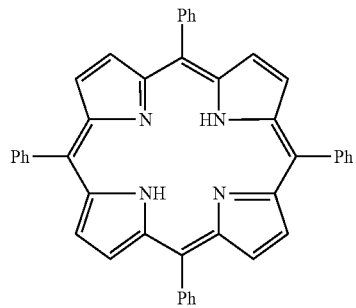 [SMILES: C1=Cc2nc1c(-c1ccccc1)c1ccc([nH]1)c(-c1ccccc1)c1nc(c(-c3ccccc3)c3ccc([nH]3)c2-c2ccccc2)C=C1]

Reaction of substituted Tetraphenyl porphyrin Photocatalyst 180 with chlorosilyl ester 8 gives substituted Tetraphenyl-porphyrin Photocatalyst Composition 181.

Reaction of Tetraphenyl Porphyrin photocatalyst 182 with aminosilyl ester 4 gives Tetraphenyl-porphyrin Photocatalyst Composition 183. Reaction of Tetraphenyl-porphyrin Photocatalyst 182 with mercaptosilyl ester 5 gives substituted Tetraphenyl Porphyrin Photocatalyst Composition 184.

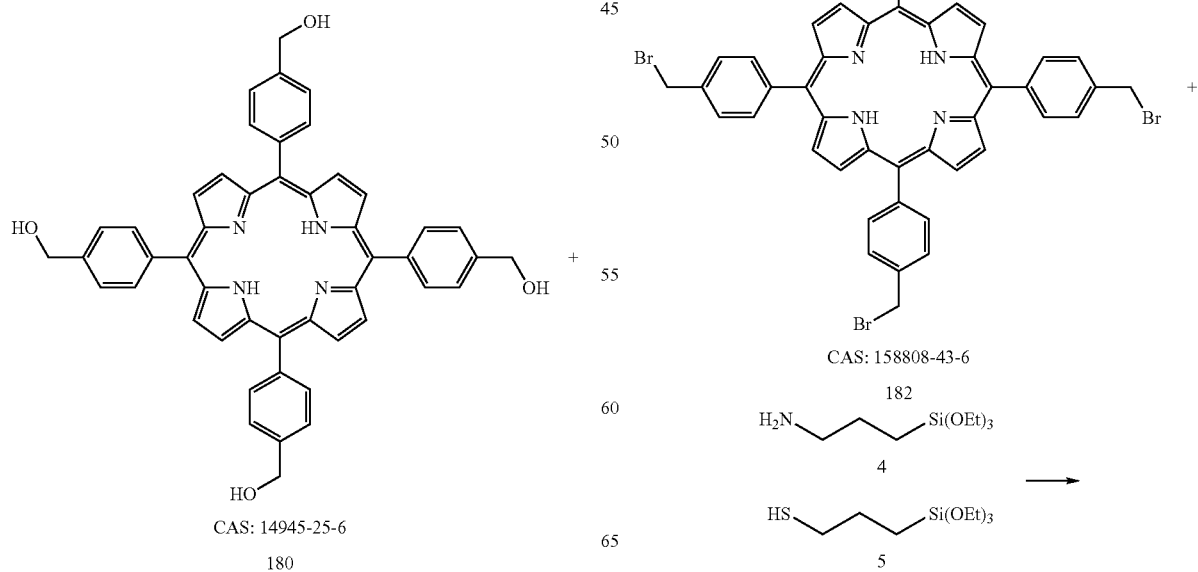

EXAMPLE 42
Metallo-Tetraphenyl porphyrin; Φ~0.6-0.9
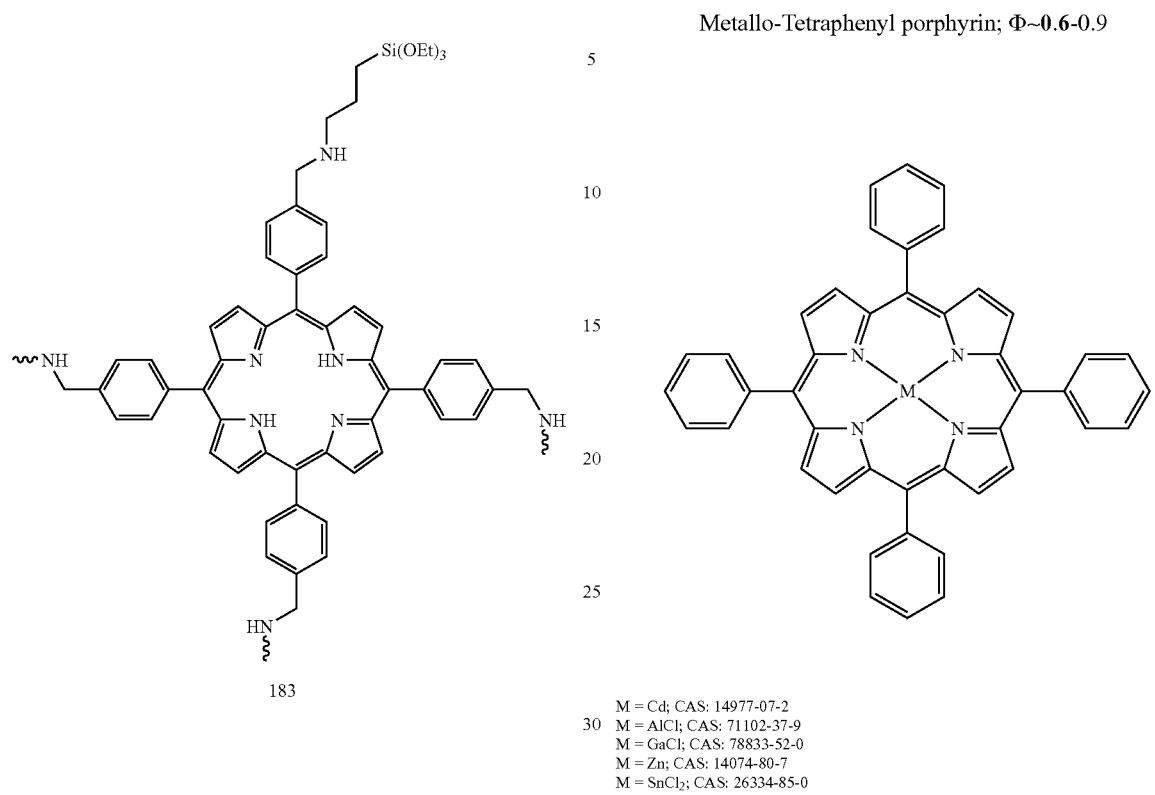
M = Cd; CAS: 14977-07-2
M = AlCl; CAS: 71102-37-9
M = GaCl; CAS: 78833-52-0
M = Zn; CAS: 14074-80-7
M = SnCl$_2$; CAS: 26334-85-0
Reaction of substituted Metallo-Tetraphenyl Porphyrin photocatalyst 185 with chlorosilyl ester 8 gives substituted Metallo-Tetraphenyl Porphyrin Photocatalyst Composition 186.
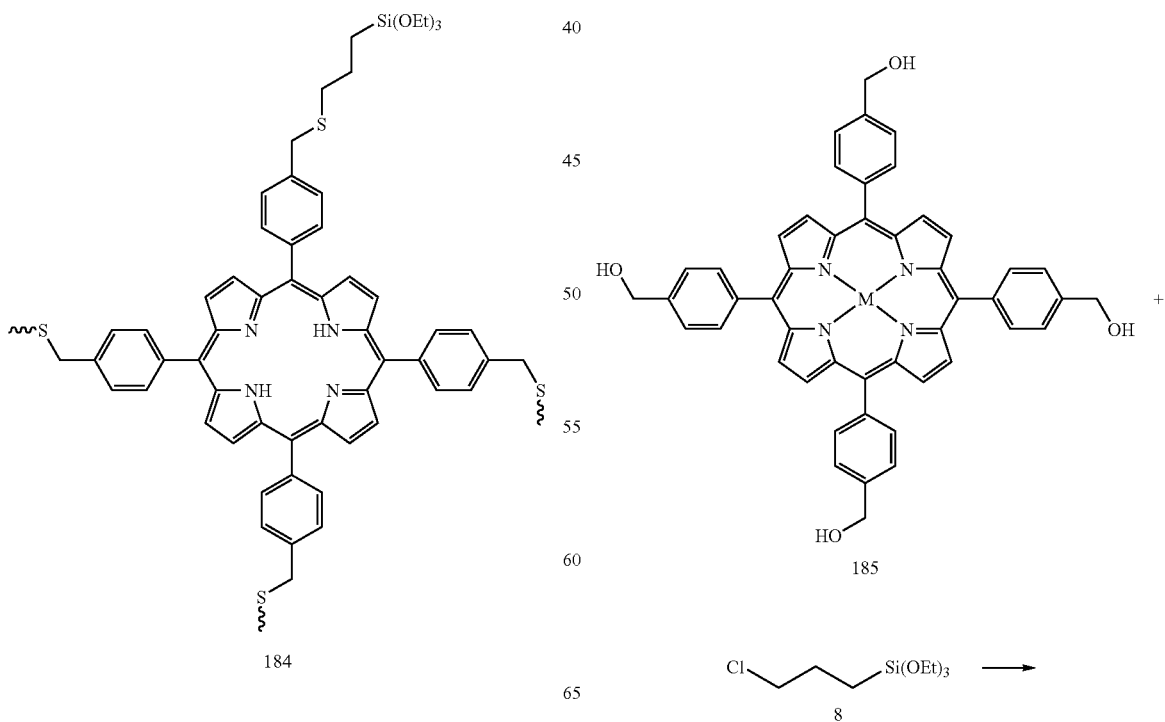

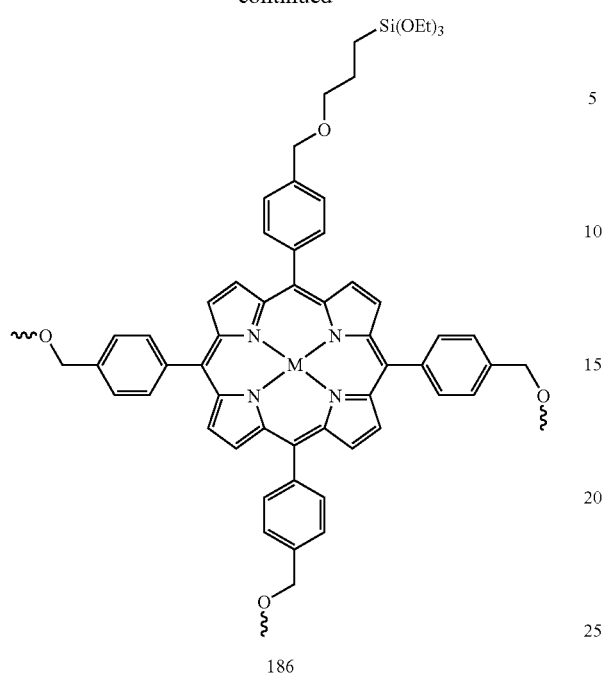

186

M = Cd; CAS: 14977-07-2
M = AlCl; CAS: 71102-37-9
M = GaCl; CAS: 78833-52-0
M = Zn: CAS: 14074-80-7
M = SnCl$_2$; CAS: 26334-85-0

Reaction of substituted Metallo-Tetraphenyl Porphyrin Photocatalyst 187 with aminosilyl ester 4 gives substituted Metallo-Tetraphenyl Porphyrin Photocatalyst Composition 188. Reaction of substituted Metallo-Tetraphenyl Porphyrin Photocatalyst 187 with mercaptosilyl ester 5 gives substituted Metallo-Tetraphenyl Porphyrin Photocatalyst Composition 189.

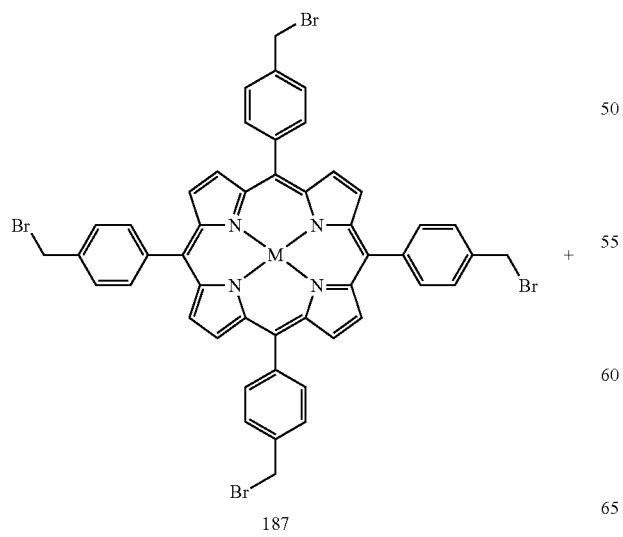

187

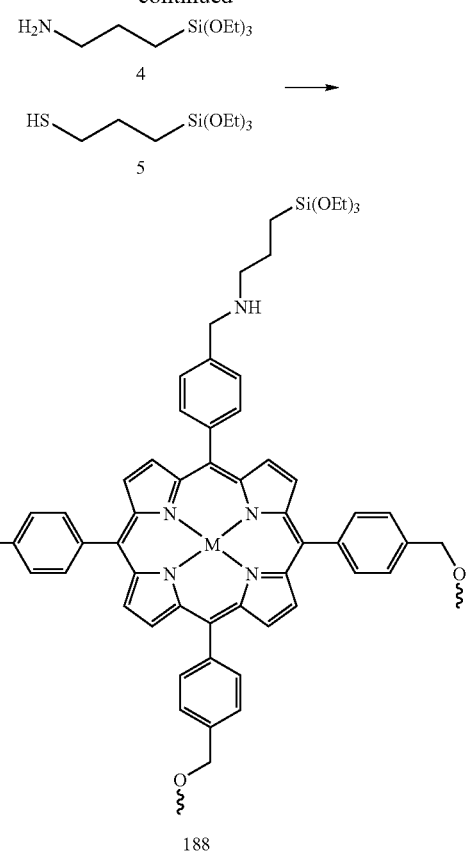

188

189

M = Cd; CAS: 14977-07-2
M = AlCl; CAS: 71102-37-9
M = GaCl; CAS: 78833-52-0
M = Zn: CAS: 14074-80-7
M = SnCl$_2$; CAS: 26334-85-0

EXAMPLE 43

Methylene Blue CAS: 61-73-4; Φ~0.5

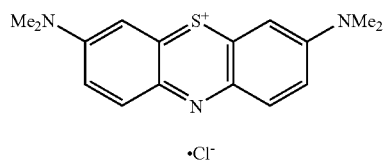

Reaction of substituted Methylene Blue Photocatalyst 195 with bromosilyl ester 196 gives substituted Methylene Blue Photocatalyst Composition 197.

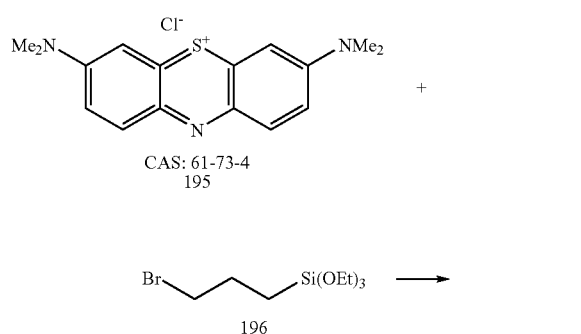

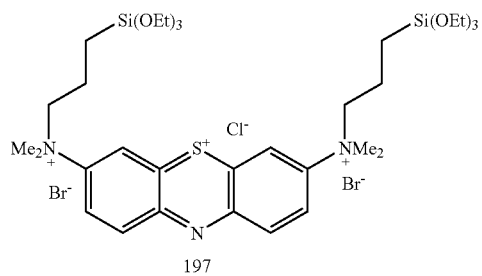

Applicant have disposed their Photocatalyst Composition III onto various substrates using conventional water-borne coating equipment and methods. The following Example 44 is presented to further illustrate to persons skilled in the art how to make and use the invention. Example 44 is not intended as a limitation, however, upon the scope of Applicants' invention.

EXAMPLE 44

Tetrasulfonylchloride-substituted Aluminum Phthalocyanine Photocatalyst 190 (0.2 gram) was dissolved in ethanol (200 proof; 10 mL). Sonication was used. Triethylamine (0.08 g) was added to the photocatalyst 190 solution. Aminopropyl triethoxysilane, Compound 4, was (0.14 g) was added to the photocatalyst solution to form Photocatalyst Composition 191. The Photocatalyst Composition 191 was stirred at room temperature in the dark for 3 hrs.

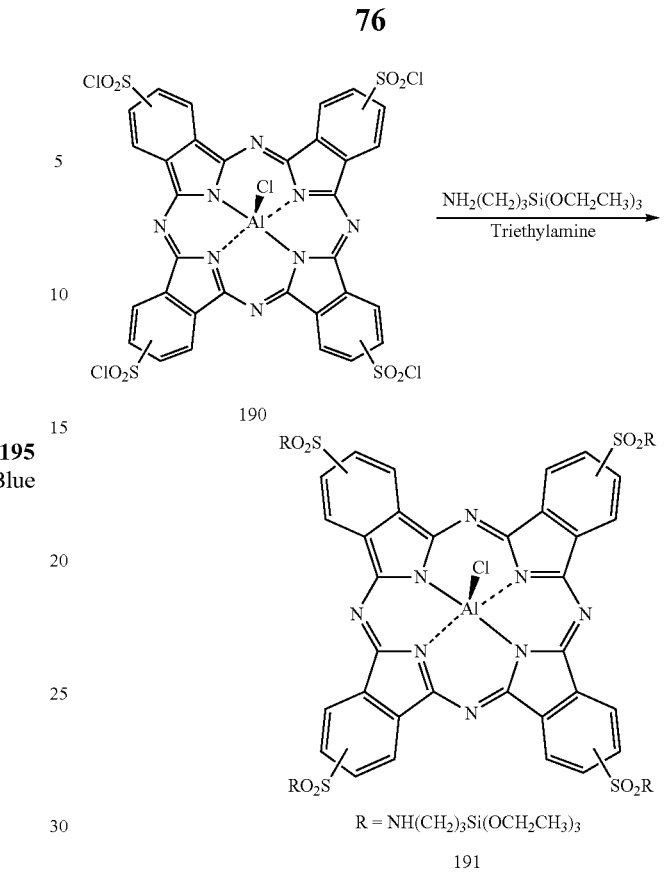

About 100 mL of 5% v/v ammonium hydroxide solution was prepared using concentrated ammonium hydroxide by mixing about 95 mL of water and 5 mL of concentrated ammonium hydroxide solution. In various embodiments, Applicants prepared a coating composition comprising between about 5% to about 25% v/v of the above-described ethanol/triethylamine solution of Photocatalyst Composition 191 in ammonium hydroxide. Table 1 recites typical formulations.

TABLE 1

| Batch No. | Dye Stock (mL) | EtOH (mL) | 5% NH$_4$OH (mL) | EtOH content |
|---|---|---|---|---|
| 1 | 0.5 | 0 | 9.5 | 5% |
| 2 | 0.5 | 2 | 7.5 | 25% |
| 3 | 1 | 0 | 9 | 10% |
| 4 | 1 | 1.5 | 7.5 | 25% |

In embodiments wherein Applicants' coating composition further comprises one or more singlet oxygen traps, those singlet oxygen trap compounds are added to the above-described ethanol/triethylamine/ammonium hydroxide mixture of Photocatalyst Composition 191. In certain embodiments described hereinbelow, Applicants' singlet oxygen scavengers comprise substituted pyridones.

Applicants' coating composition can be applied to various surfaces, including for example and without limitation polypropylene fabric, cotton fabric, nylon fabric, and the like. In this Example 43 Spunbond polypropylene sold in commerce by Kappler under the tradename Provent 1000 was employed as a coating substrate. The coating substrate was first pre-treated with a polyurethane pre-coating. For example and without limitation, WitCoBond UCX-281F sold in commerce by Chemtura was applied to the Provent 1000 surface in a 5% to about 10% w/w aqueous mixture. The polyurethane pre-coating was applied by either rolling or spraying. After application of the polyurethane pre-coating, the pre-coated Provent 1000 was allowed to dry at ambient condition overnight.

The above-described coating composition was then applied to the polyurethane precoated Provent 1000 by either rolling or spraying. The treated surface was dried at 100° C. for 1 to-2 minutes.

In certain embodiments, Applicants' coating composition comprises one or more embodiments of Photocatalyst Composition III in combination with one or more singlet oxygen scavengers, i.e. compounds that releaseably trap singlet oxygen. Applicants have found that N-substituted-2-pyridones 10 trap singlet oxygen upon irradiation in the presence of Photocatalyst Composition III and ambient oxygen to give 1,4-endoperoxides 15. Applicants have further found that such N-substituted-2-pyridonyl endoperoxides 15 efficiently release singlet oxygen over time.

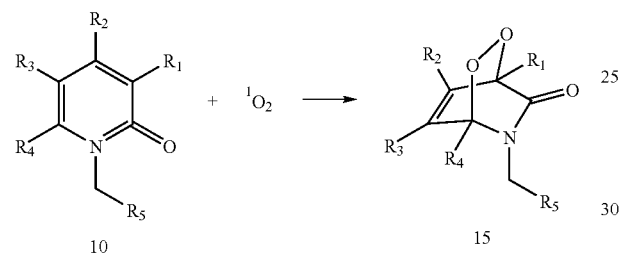

Applicants have prepared and tested N-substituted-2-pyridones 200A, 200B, 200C, 200D, 300A, 300B, and 300C, to determine the efficacy of using these compounds as singlet oxygen scavengers.

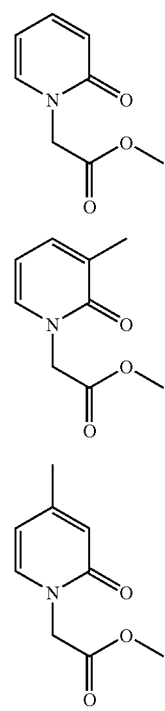

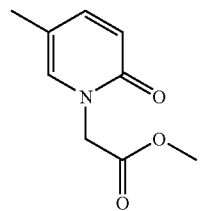
200D

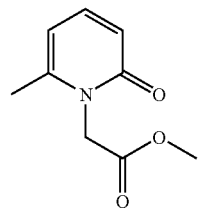
200E

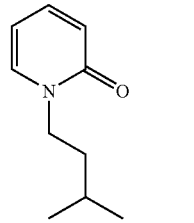
300A

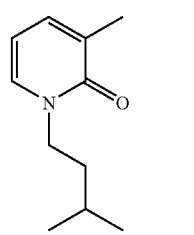
300B

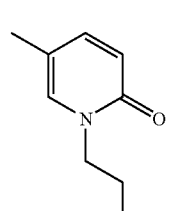
300C

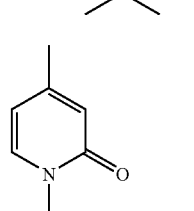
300D

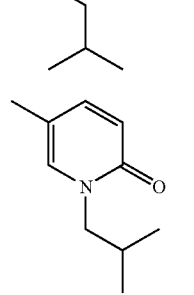
400A

Applicants have experimentally determined quantitative data on the singlet oxygen trap-release process of N-methylester substituted pyridones 200A, 200B, 200C, 200D, 200E, and N-isoamyl-2-methylpyridones 300A, 300B, 300C, 300D, and N-isobutyl-2-methylpyridone 400A. All pyridones were purified by column chromatography prior to testing.

Mixtures of each pyridone in combination with tetraphenyl porphyrin ("TPP") were prepared in chloroform. UV-Vis absorption spectrum of each individual solution and the mixture were recorded.

The mixture solution in a quartz cuvette was sealed with a silicone septum screw cap. The solution was irradiated by a Xe arc lamp (150 W) through a FSQ-RG495 filter (yellow; λ>495 nm) and a hot mirror (IR filter). The cuvette sample was located 2 feet away from the lamp housing. A fine stream oxygen (Omega micro flow meter; flow read at 10; 0.342 ml/min) was bubbled to the solution during irradiation. The consumptions of the pyridones were monitored by UV-Vis absorption spectroscopy at their $\lambda_{max}$ 260-340 nm.

The irradiated solution was subsequently allowed to sit in a temperature control cell holder in the dark at 40° C. for 1 min before the absorption spectrum of the solution at 40° C. was recorded. The regeneration of each pyridones was monitored by recording change in its $\lambda_{max}$, as a function of time.

When two individual compounds have overlapped absorption bands, as shown by Equation (1) an absorbance at a particular wavelength in a mixture equals to a summation of absorbances from each individual component at that wavelength.

$$A_m = \epsilon_1 b C_1 + \epsilon_2 b C_2 \qquad (1)$$

The thermal decomposition of the endoperoxide adducts were expected to follow a first order reaction kinetics. Thus, the integrated rate law is expressed using equations (2) and (3):

$$1^{st} \text{ order; } [\text{Endo}]_t = [\text{Endo}]_0 \, e^{-kt} \qquad (2)$$

$$\ln [\text{Endo}]_t = -kt + \ln[\text{Endo}]_0 \qquad (3)$$

The progress of Endoperoxide release reaction was monitored by the increase of the pyridone absorption, thus the concentrations of the endoperoxide at various reaction times can be calculated by equations (4) and (5).

$$[\text{Endo}]_t = [\text{Endo}]_0 - [\text{Pyridone}]_t \qquad (4)$$

$$[\text{Pyridone}]_t = A_{(pyridone)} / \epsilon_{pyridone} \qquad (5)$$

TABLE 2 through 11 recite kinetic data for both the formation of an Endoperoxide from a substituted pyridone, and for the deposition of that Endoperoxide to regenerate singlet oxygen. The measured half lives for the 10 endoperoxides studied varied from about 1 hour to about 9.6 hours.

TABLE 2

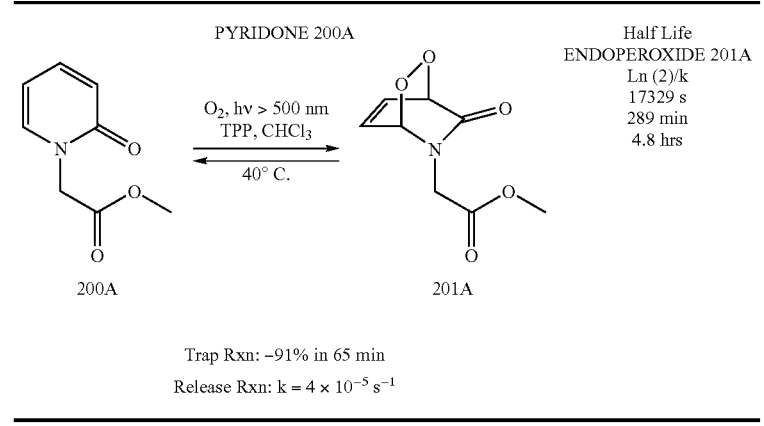

Trap Rxn: ~91% in 65 min

Release Rxn: k = 4 × 10⁻⁵ s⁻¹

TABLE 3

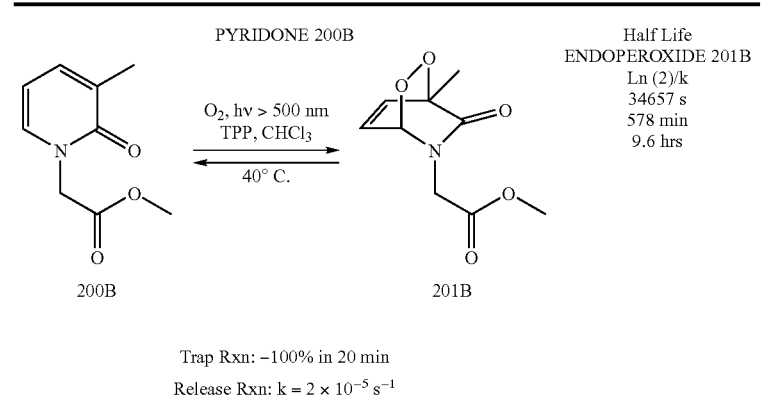

Trap Rxn: ~100% in 20 min

Release Rxn: k = 2 × 10⁻⁵ s⁻¹

TABLE 4
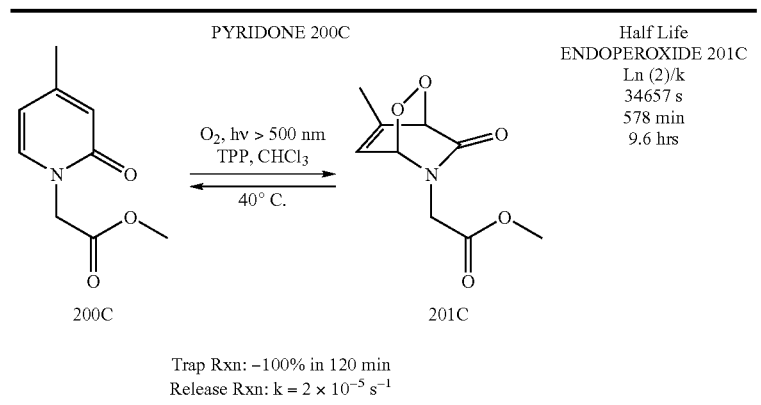
Half Life
ENDOPEROXIDE 201C
Ln (2)/k
34657 s
578 min
9.6 hrs
Trap Rxn: ~100% in 120 min
Release Rxn: k = 2 × 10$^{-5}$ s$^{-1}$
TABLE 5
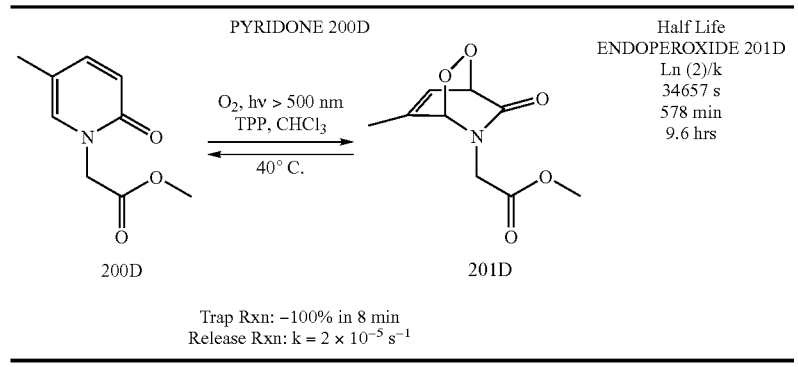
Half Life
ENDOPEROXIDE 201D
Ln (2)/k
34657 s
578 min
9.6 hrs
Trap Rxn: ~100% in 8 min
Release Rxn: k = 2 × 10$^{-5}$ s$^{-1}$
TABLE 6
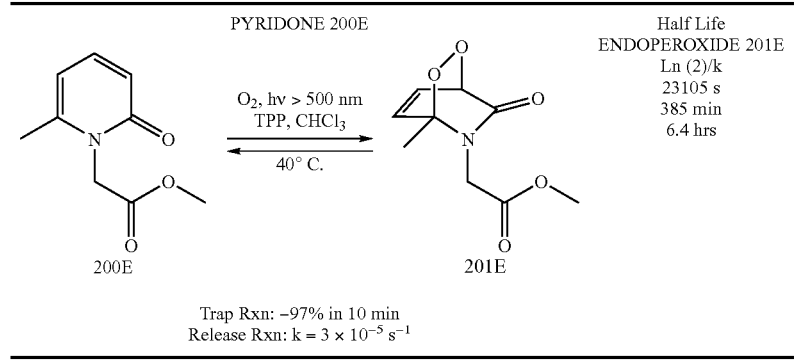
Half Life
ENDOPEROXIDE 201E
Ln (2)/k
23105 s
385 min
6.4 hrs
Trap Rxn: ~97% in 10 min
Release Rxn: k = 3 × 10$^{-5}$ s$^{-1}$
TABLE 7
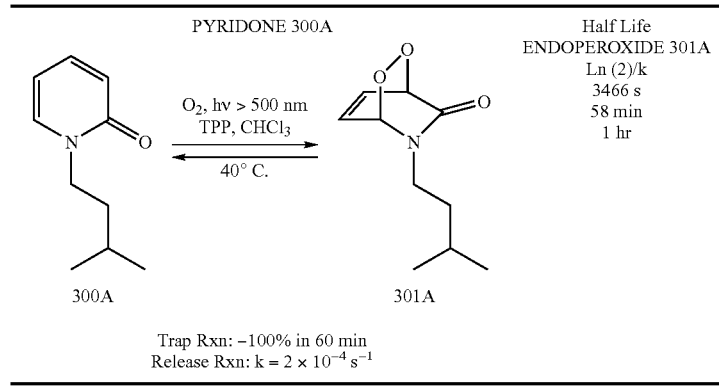
Half Life
ENDOPEROXIDE 301A
Ln (2)/k
3466 s
58 min
1 hr
Trap Rxn: ~100% in 60 min
Release Rxn: k = 2 × 10$^{-4}$ s$^{-1}$

TABLE 8

PYRIDONE 300B ⇌ (O₂, hv > 500 nm; TPP, CHCl₃; 40° C.) ENDOPEROXIDE 301B

Half Life
Ln (2)/k
7702 s
128 min
2.1 hrs

300B → 301B

Trap Rxn: ~96% in 6 min
Release Rxn: k = 9 × 10⁻⁵ s⁻¹

TABLE 9

PYRIDONE 300C ⇌ (O₂, hv > 500 nm; TPP, CHCl₃; 40° C.) ENDOPEROXIDE 301C

Half Life
Ln (2)/k
6931 s
116 min
1.9 hrs

300C → 301C

Trap Rxn: ~100% in 6 min
Release Rxn: k = 1 × 10⁻⁴ s⁻¹

TABLE 10

PYRIDONE 300D ⇌ (O₂, hv > 500 nm; TPP, CHCl₃; 40° C.) ENDOPEROXIDE 301D

Half Life
Ln (2)/k
11552 s
193 min
3.2 hrs

300D → 301D

Trap Rxn: ~90% in 30 min
Release Rxn: k = 6 × 10⁻⁵ s⁻¹

TABLE 11

PYRIDONE 400A ⇌ (O₂, hv > 500 nm; TPP, CHCl₃; 40° C.) ENDOPEROXIDE 401A

Half Life
Ln (2)/k
11552 s
193 min
3.2 hrs

400D → 401D

Trap Rxn: ~99.1% in 5 min
Release Rxn: k = 6 × 10⁻⁵ s⁻¹

Figure 2:
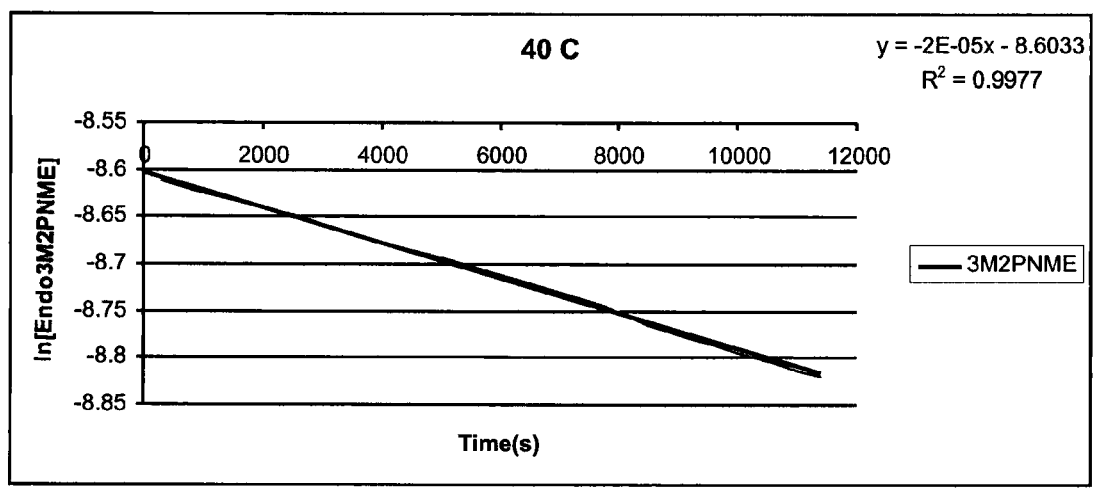
FIG. 2 graphically shows the rate of decomposition of a second Endoperoxide compound to release singlet oxygen.
Figure 3:
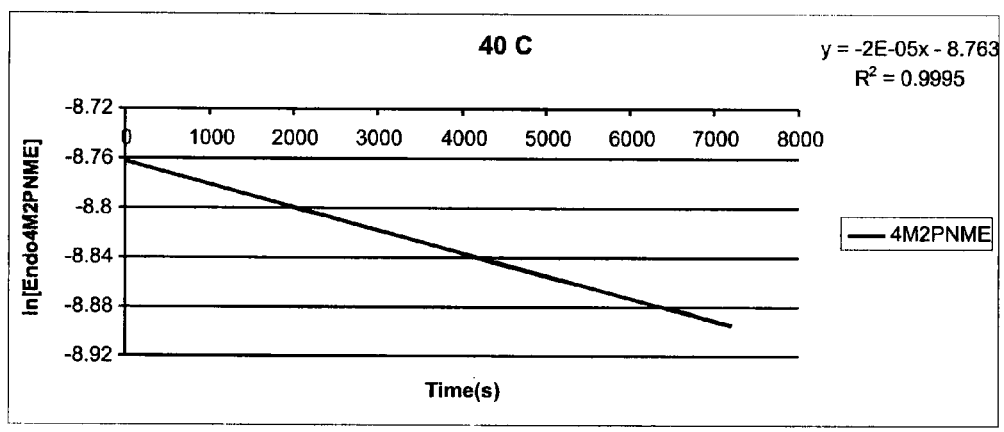
FIG. 3 graphically shows the rate of decomposition of a third Endoperoxide compound to release singlet oxygen.
Figure 4:
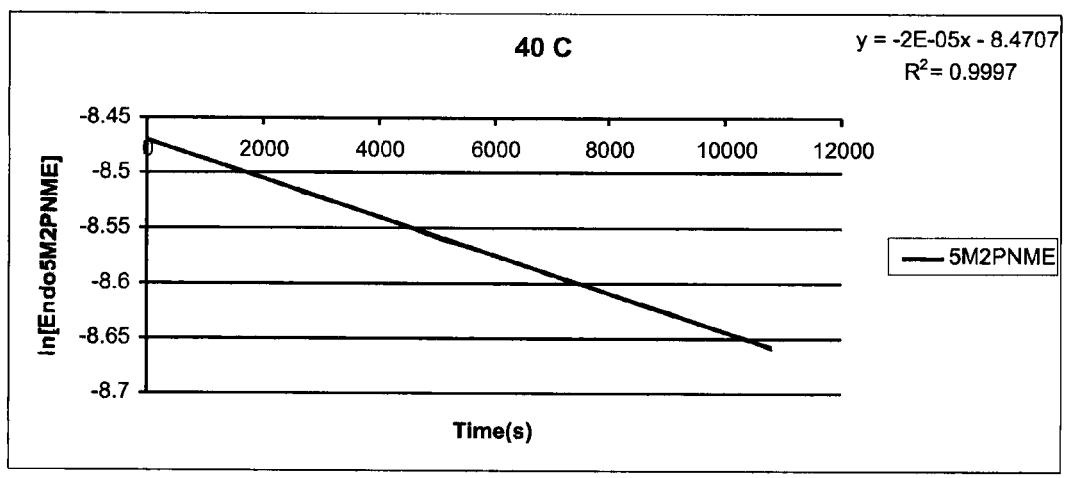
FIG. 4 graphically shows the rate of decomposition of a fourth Endoperoxide compound to release singlet oxygen.
Figure 5:
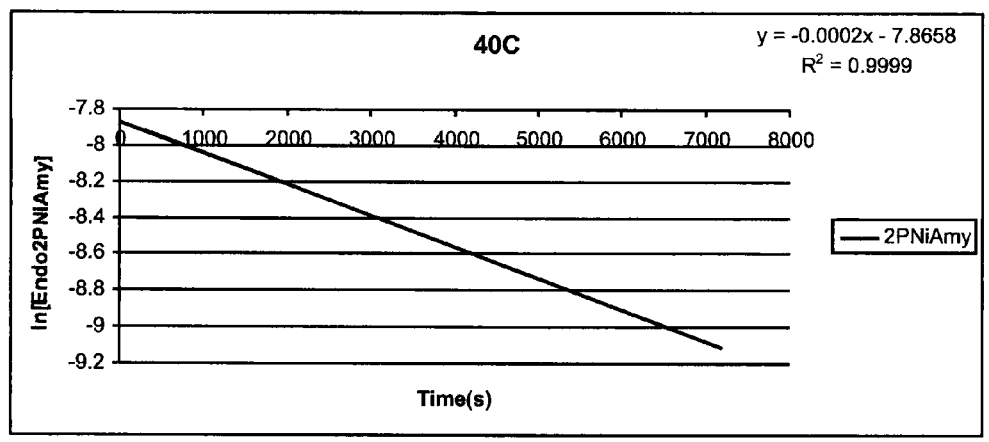
FIG. 5 graphically shows the rate of decomposition of a fifth Endoperoxide compound to release singlet oxygen.
Figure 6:
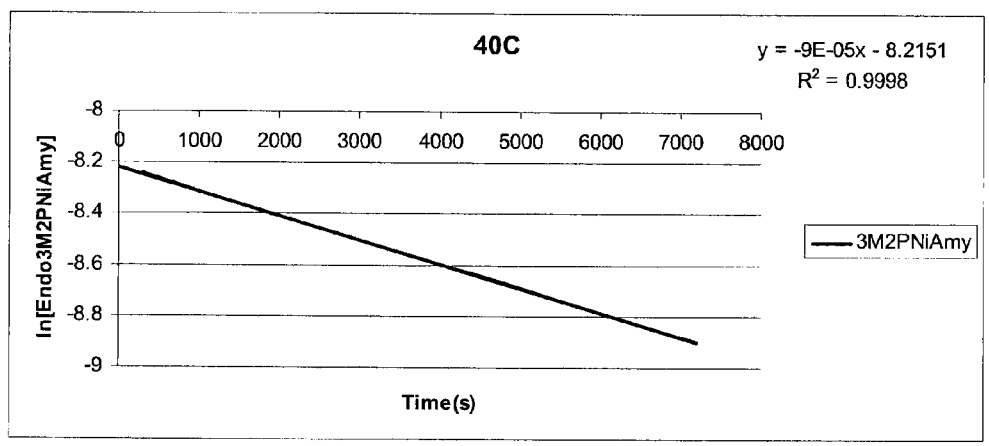
FIG. 6 graphically shows the rate of decomposition of a sixth Endoperoxide compound to release singlet oxygen.
Figure 7:
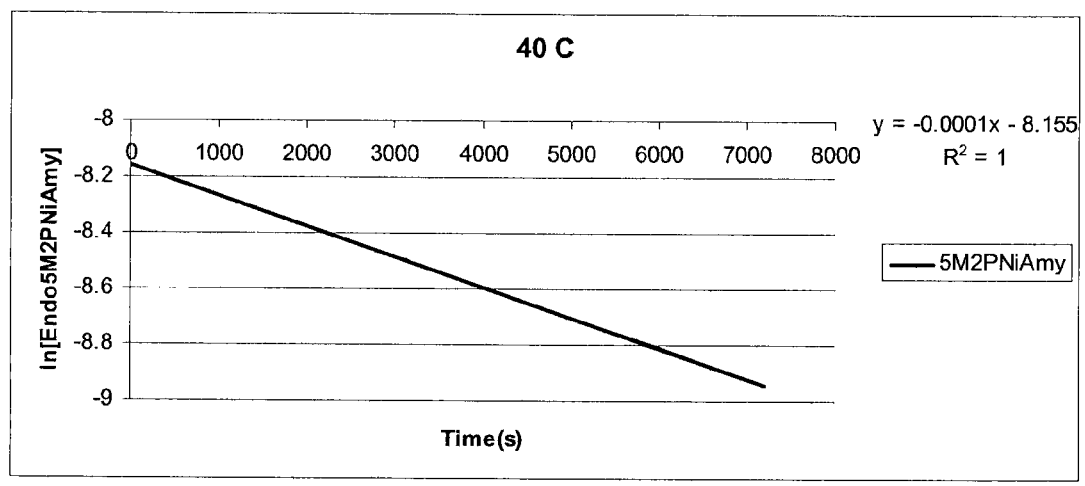
FIG. 7 graphically shows the rate of decomposition of a seventh Endoperoxide compound to release singlet oxygen.
Figure 8:
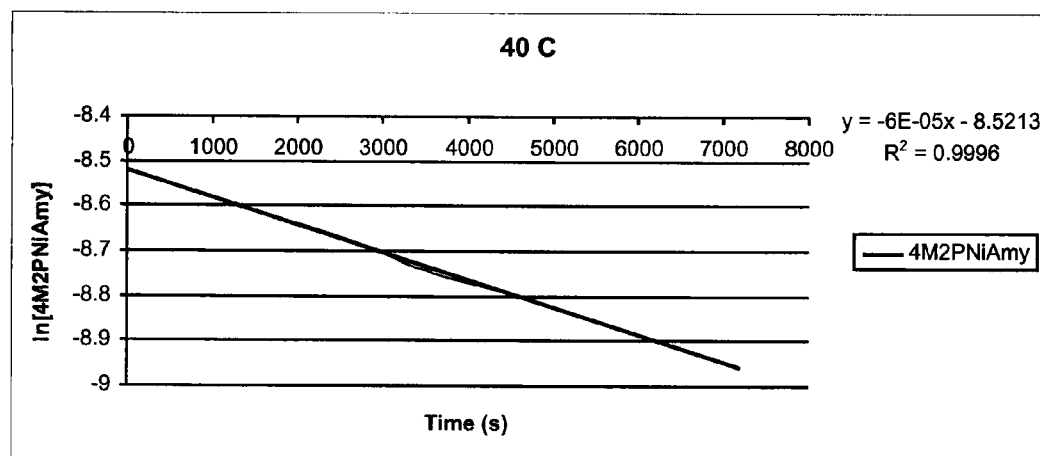
FIG. 8 graphically shows the rate of decomposition of an eighth Endoperoxide compound to release singlet oxygen.
Figure 9:
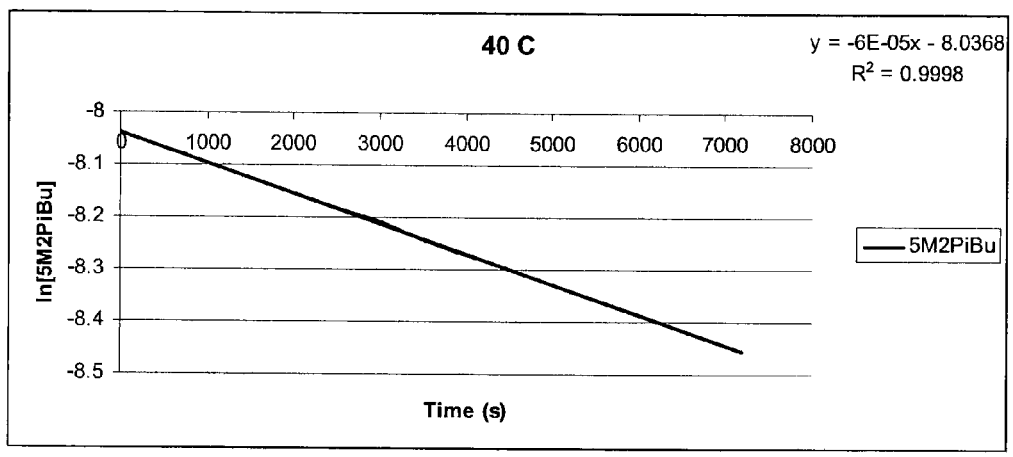
FIG. 9 graphically shows the rate of decomposition of a ninth Endoperoxide compound to release singlet oxygen.
Figure 10:
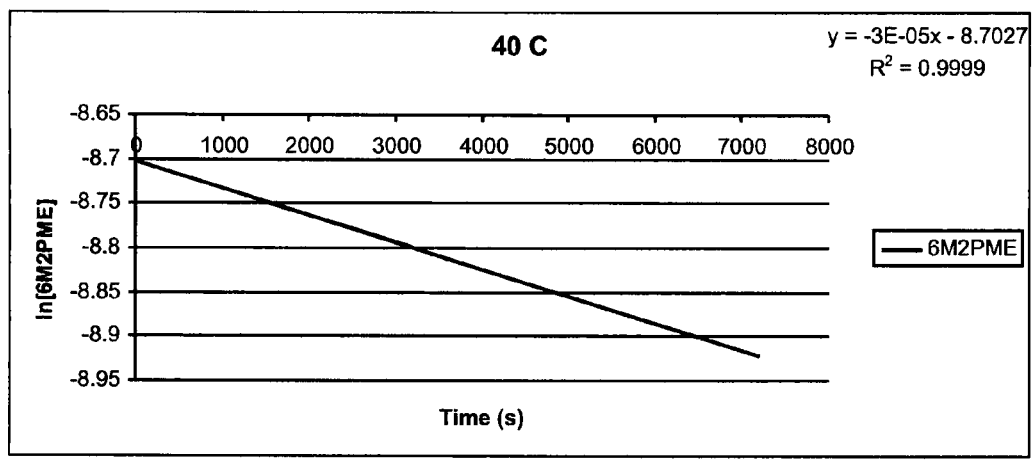
FIG. 10 graphically shows the rate of decomposition of a tenth Endoperoxide compound to release singlet oxygen.

FIGS. 1 through 10 illustrate plots between 1n[Endoperoxide] Vs time (sec). Each plot clearly shows a linear relationship which indicates that the decomposition of each endoperoxide obeys first order reaction kinetics. Applicants' rate studies show that a methyl group substituted on the pyridone ring at position 3 and 5 improves singlet oxygen trap kinetics by approximately 3 and 10 times, respectively. In contrast, substitution of a methyl group at the pyridone ring position 4 deactivates the singlet oxygen trap of the pyridones.

Substitution of a sterically hindraning group at the N-atom of the pyridones exhibited an increase in decomposition rate of the endoperoxides. Substitution of an iso-amyl group at the N-atom of the pyridones increases the releasing kinetics by approximately 5 times faster than substitution with a methyl ester group. The best performing pyridone in both singlet oxygen trap and release is 5-methyl-N-isoamyl-2-pyridone.

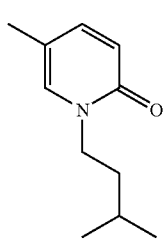

Applicants have modified their substituted pyridone compounds to comprise pendent silyl ester groups. As an example, reacting substituted pyridone 300C with N-Bromosuccinimide in chloroform gives bromonated, substituted pyridone 305C. Reaction of brominated, substituted pyridone 305C with mercapto silyl ester 7 gives substituted N-isoamyl pyridone 310C, wherein pyridone 310C comprises a pendent silyl ester group.

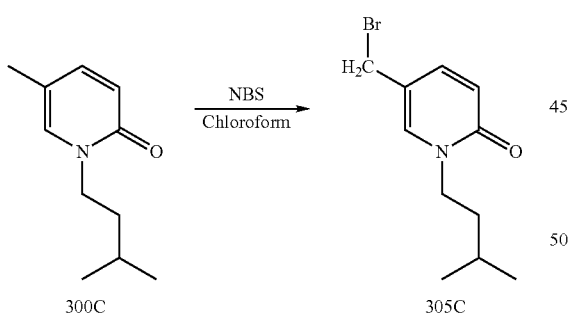

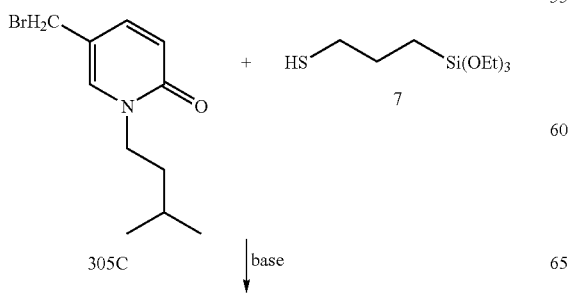

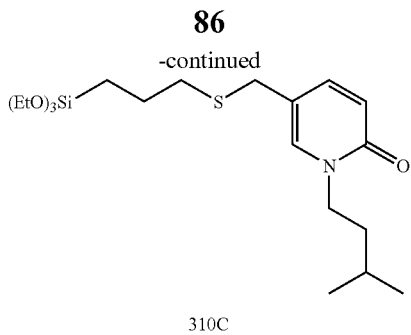

Similarly, substituted pyridones 200B, 200C, 200D, 200E, 300B, 300D, and 400A, can be modified to form substituted pyridones 210B, 210C, 210D, 210E, 310B, 310D, and 410A, each comprising a pendent silyl ester group.

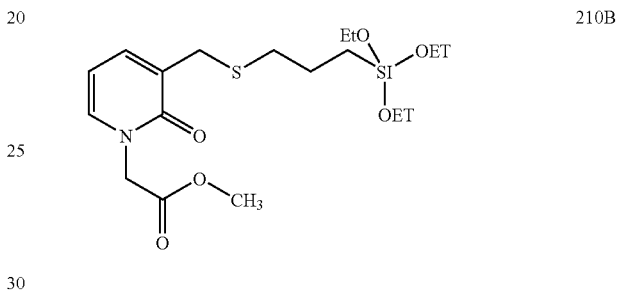

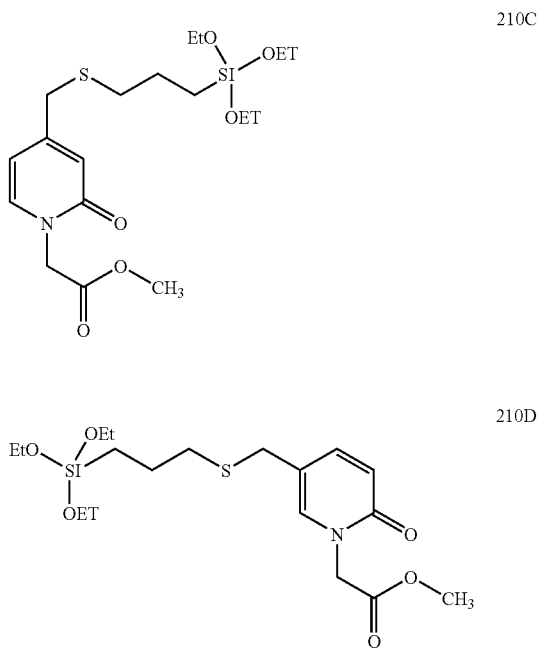

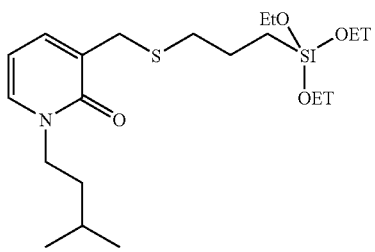

310B

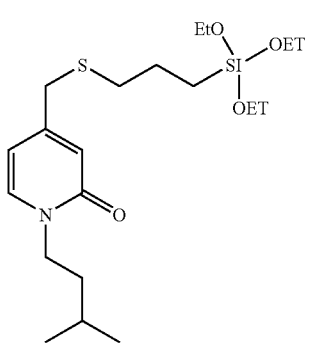

310D

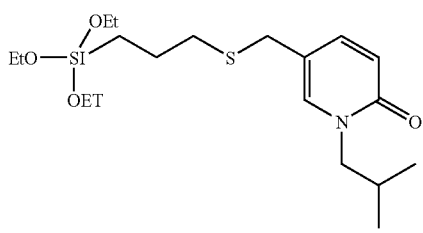

410A

Applicants reacted substituted pyridone 200A with amino silyl ester 4 to form pyridone 210A comprising a pendent silyl ester group.

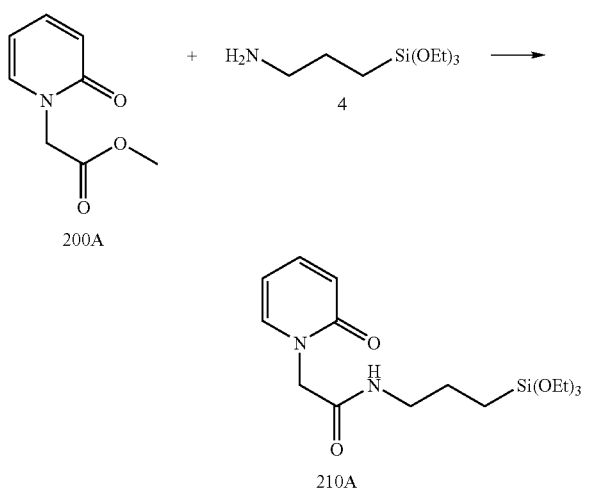

Similar chemistry can be used to form pendent silyl ester containing pyridones 215B, 215C, 215D, and 215E.

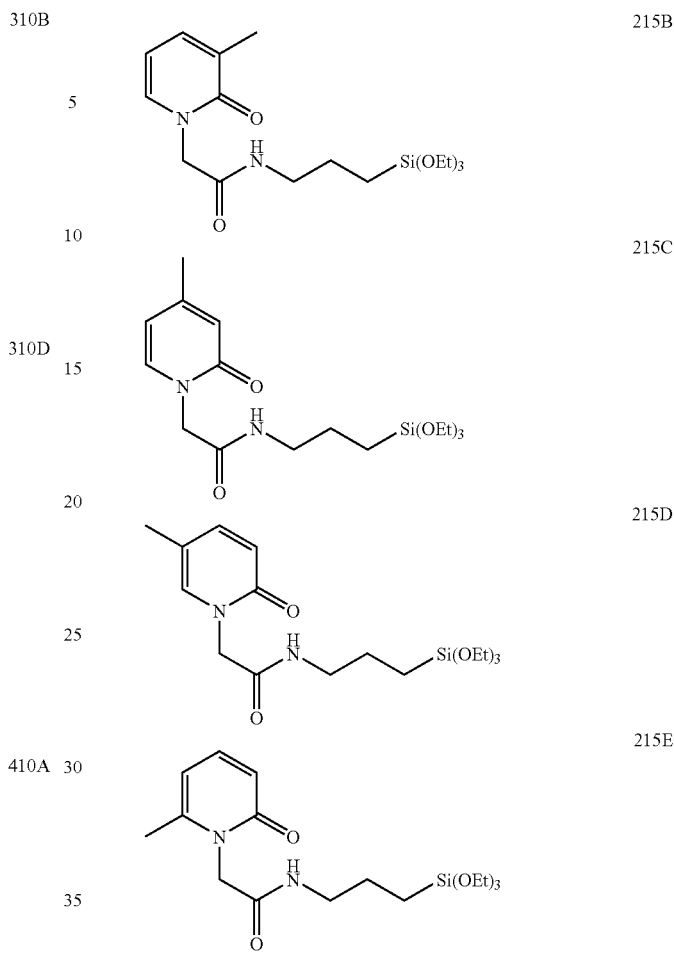

In certain embodiments, Applicants' coating composition comprises one or more of silyl ester substituted pyridones 210A, 210B, 215B, 210C, 215C, 210D, 215D, 210E, 215E, 310B, 310D, and/or 410A, in combination with Applicants' ethanolic/triethylamine/Photocatalyst Composition III mixture. In certain embodiments, the one or more N-methylester substituted pyridones silyl ester substituted pyridones 210A, 210B, 215B, 210C, 215C, 210D, 215D, 210E, 215E, 310B, 310D, and/or 410A, are present from about 0.10 to about 50 molar excess based upon the moles of Photocatalyst III present in the coating composition.

The resulting coating generates singlet oxygen when exposed to both ambient air and light. Applicants have found that both sunlight and artificial light, i.e. both incandescent and/or fluorescent, effectively cause a coating comprising one or more embodiments of Applicants' Photocatalyst Composition III to generate singlet oxygen. When a fabric/substrate bearing a coating comprising one or more embodiments of Applicants' Photocatalyst Compositions in combination with one or more endoperoxides formed from silyl ester substituted pyridones 210B, 210C, 210D, 210E, 310B, 310D, and/or 410A, is disposed in a dark environment such that the one or more Photocatalyst Composition III moieties do not generate singlet oxygen, the one or more endoperoxides decompose to release singlet oxygen, wherein those one or more endoperoxides have the half lives recited in Tables 2 through 11.

The substituted pyridone singlet oxygen traps used in any coating formulation are selected based upon the anticipated hours of darkness that a fabric/substrate coated with Applicants' Photocatalyst Composition/Pyridone coating will experience. For example, where a 1-2 hour period of darkness is anticipated, then the fabric/substrate will be coated with a coating comprising one or more embodiments of Applicants' Photocatalyst Composition in combination with one or more of substituted pyridone 310C. Where a 2-4 hour period of darkness is anticipated, then the fabric/substrate will be coated with a coating comprising one or more embodiments of Applicants' Photocatalyst Composition III in combination with one or more of substituted pyridones 310B, 310D, and/or 410A. Where a 4-6 hour period of darkness is anticipated, then the fabric/substrate will be coated with a coating comprising one or more embodiments of Applicants' Photocatalyst Composition in combination with one or more of substituted pyridones 210E, 310D, and/or 410A. Where a 6-10 hour period of darkness is anticipated, then the fabric/substrate will be coated with a coating comprising one or more embodiments of Applicants' Photocatalyst Composition in combination with one or more of substituted pyridones 210B, 210C, 210D, and/or 210E. Where a period of darkness greater than 10 hours is anticipated, then the fabric/substrate will be coated with a coating comprising one or more embodiments of Applicants' Photocatalyst Composition in combination with one or more of substituted pyridones 210B, 210C, and/or 210D.

While the preferred embodiments of the present invention have been illustrated in detail, it should be apparent that modifications and adaptations to those embodiments may occur to one skilled in the art without departing from the scope of the present invention as set forth in the following claims.

We claim:

1. A coating composition, comprising a photocatalyst composition comprising a phthalocyanine photocatalyst molecule to convert ambient oxygen to singlet oxygen in the presence of light, wherein said photocatalyst molecule comprises a pendent silyl ester group and an Al—Cl moiety.

2. The coating composition of claim 1, wherein said photocatalyst molecule comprises a porphyrin.

3. The coating composition of claim 1, further comprising an N-substituted pyridone.

4. The coating composition of claim 3, wherein said N-substituted pyridone comprises an N-isoamyl pyridone.

5. The coating composition of claim 3, wherein said N-substituted pyridone comprises an N-isobutyl pyridone.

6. The coating composition of claim 3, wherein said pyridone compound comprises an N-(methylacetoxy)-pyridone.

7. The coating composition of claim 3, wherein said N-substituted pyridone further comprises a 3-methyl-N-substituted pyridone.

8. The coating composition of claim 3, wherein said N-substituted pyridone further comprises a 5-methyk-N-substituted pyridone.

9. The coating composition of claim 3, wherein said N-substituted pyridone comprises a pendent silyl ester group.

* * * * *